(12) United States Patent
Mutz

(10) Patent No.: US 8,436,030 B2
(45) Date of Patent: May 7, 2013

(54) POLYMORPHIC FORMS OF DEFERASIROX (ICL670A)

(75) Inventor: Michael Mutz, Freiburg (DE)

(73) Assignee: Navartis AG, Basel (CH)

( * ) Notice: Subject to any disclaimer, the term of this patent is extended or adjusted under 35 U.S.C. 154(b) by 26 days.

(21) Appl. No.: 13/405,428

(22) Filed: Feb. 27, 2012

(65) Prior Publication Data

US 2012/0203007 A1 Aug. 9, 2012

Related U.S. Application Data

(62) Division of application No. 12/515,743, filed as application No. PCT/EP2007/062903 on Nov. 27, 2007, now Pat. No. 8,153,672.

(30) Foreign Application Priority Data

Nov. 29, 2006 (EP) ................................. 06125002
Jul. 19, 2007 (EP) ................................. 07112795

(51) Int. Cl.
*A61K 31/4196* (2006.01)
*C07D 249/08* (2006.01)

(52) U.S. Cl.
USPC ...................................... 514/383; 548/269.4

(58) Field of Classification Search .................. 514/383; 548/269.4
See application file for complete search history.

(56) References Cited

U.S. PATENT DOCUMENTS

| 6,723,742 B2 * | 4/2004 | Lattmann et al. ............. 514/383 |
| 2008/0262060 A1 * | 10/2008 | Toth et al. ..................... 514/383 |

FOREIGN PATENT DOCUMENTS

| EP | 0914118 A | 5/1999 |
| WO | 97/49395 | 12/1997 |
| WO | 2005/097062 A | 10/2005 |
| WO | 2006/084683 | 8/2006 |
| WO | 2006/130532 | 8/2006 |

OTHER PUBLICATIONS

Huang, Xi: "Iron overload and its association with cancer risk in humans: evidence for iron as a carcinogenic matal", Mutation Research 533 (200) 153-171, 2003.
Lou, Ji et al: "Principles of cancer therapy: oncogene and non-oncogene addiction". Cell 136:5, Mar. 6, 2009, 823-837.
Brissot, Pierre et al: "Current approach to hemochromatosis", Blood Reviews (2008) 22, 195-210.
Steinhauser, Stefan et al: "Complex formation of ICL670 and related ligands with FeIII and FeII",European Journal of Inorganic Chemistry, 21, 2004, 4177-4192.
Kalinoswki, D.S., et al: "The evolution or iron chelators for the treatment of iron overload disease and Cancer", Pharmacological Reviews, 57.4, 2005, 548-583.
McCauley J A. et al: "Detection and characterization of polymorphism in the pharmaceutical industry", Aiche symposium Series, American Institute of Chemical Engineers, New York, NY 87, 1991, 58-63.

* cited by examiner

*Primary Examiner* — Rebecca Anderson
*Assistant Examiner* — Matthew Coughlin
(74) *Attorney, Agent, or Firm* — Gregory Houghton

(57) ABSTRACT

The invention relates to crystalline forms of 4-[3,5-bis(2-hydroxyphenyl)-[1,2,4]triazol-1-yl]benzoic acid and to its amorphous form, to processes for the preparation thereof, to compositions containing the same and their uses for the manufacture of a medicament for the treatment of the human body.

8 Claims, 11 Drawing Sheets

Zoom plot between 1880cm⁻¹ – 1000cm⁻¹

Zoom plot between 1880cm$^{-1}$ – 1000cm$^{-1}$

Fig. 9 (Form C):
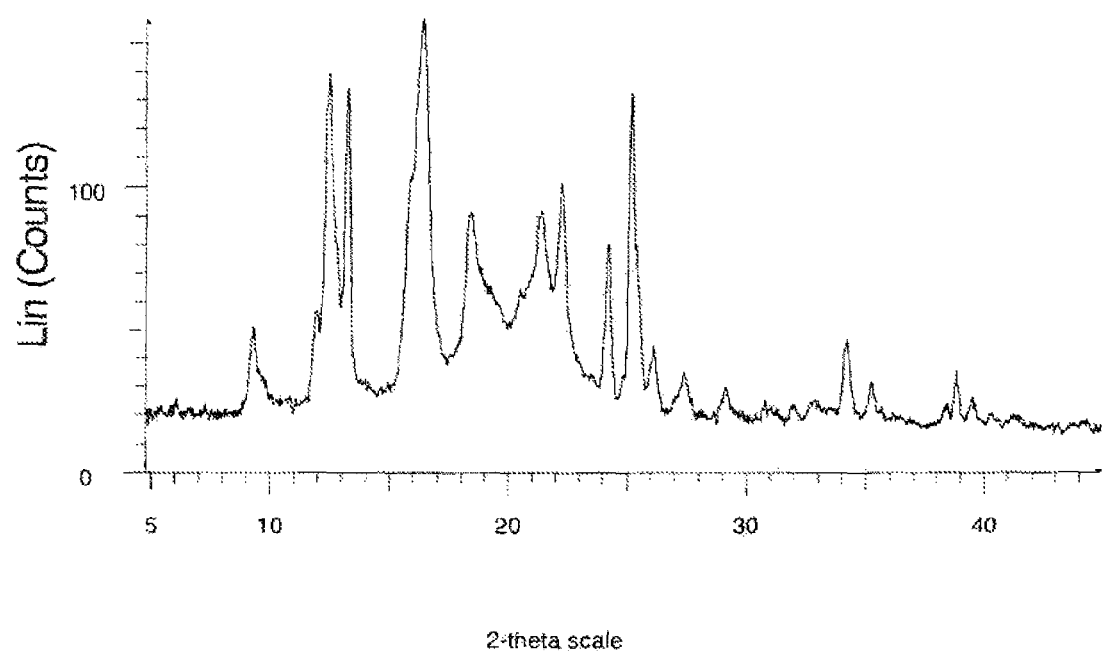

Fig. 10 (Form C):
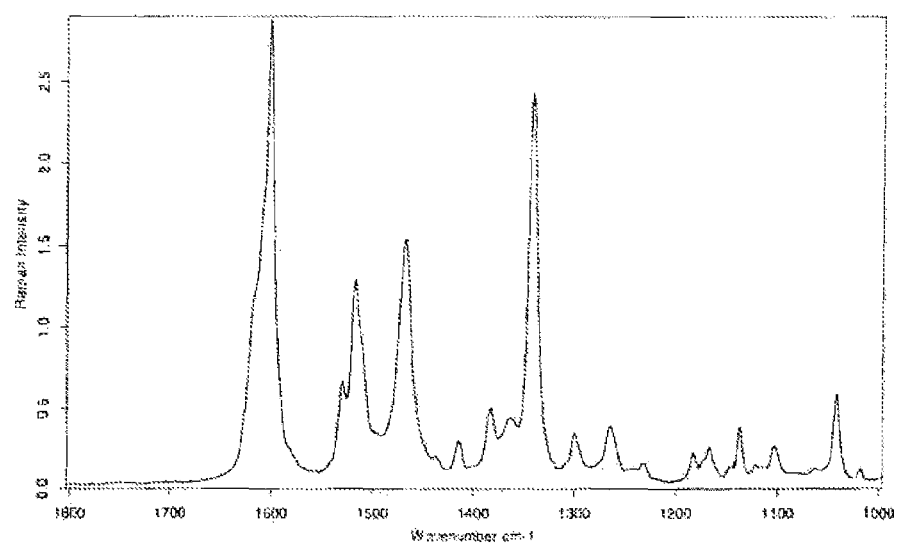
Fig. 11 (Form D):
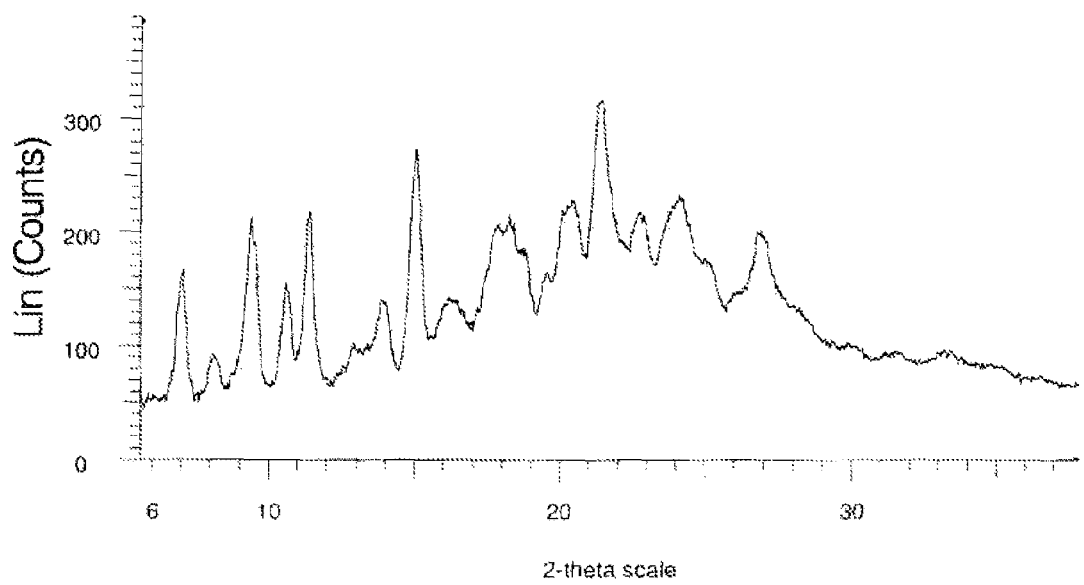

Fig. 12 (Form D):
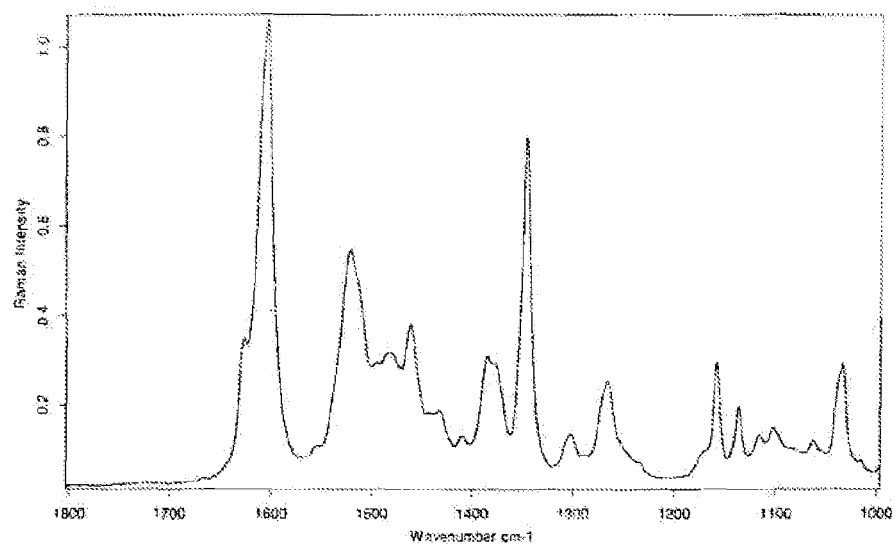
Fig. 13 (Form S_B):
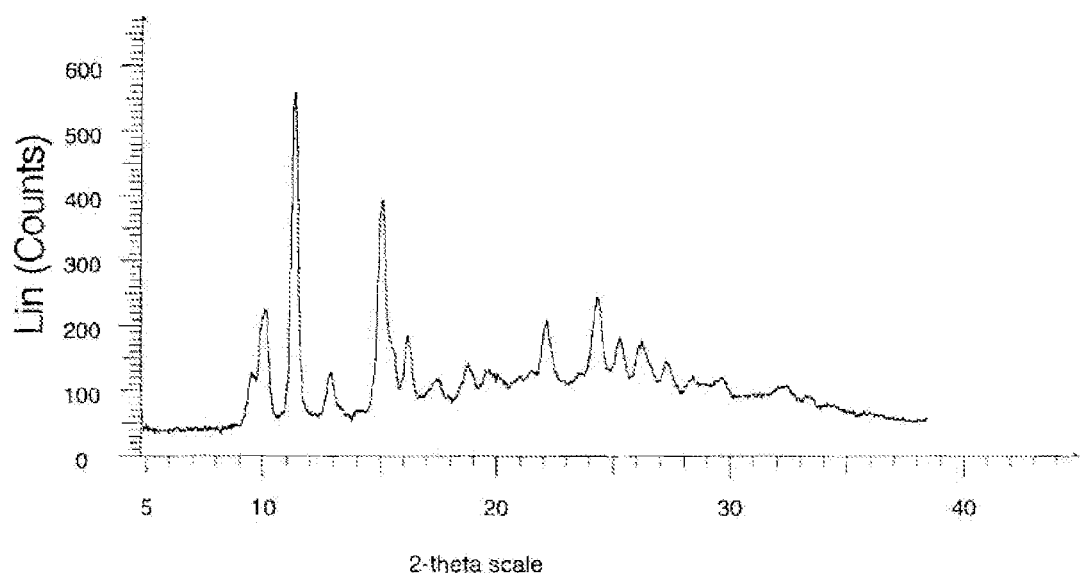

POLYMORPHIC FORMS OF DEFERASIROX (ICL670A)

This is a divisional of application Ser. No. 12/515,743 filed on May 21, 2009 now U.S. Pat. No. 8,153,672, which in its entirety is herein incorporated by reference and which is a National Stage of International Application No. PCT/EP2007/062903 filed on Nov. 27, 2007, which in its entirety is herein incorporated by reference and which claims priority under 35 U.S.C. §119 to EP Application Serial No. 06125002.3 filed Nov. 29, 2006 and EP Application Serial No. 07112795.5.

The invention relates to new crystalline forms of 4-[3,5-bis(2-hydroxyphenyl)-[1,2,4]triazol-1-yl]benzoic acid; the processes for preparation of these crystalline forms, compositions containing these crystalline forms, and the use of these crystalline forms in diagnostic methods or therapeutic treatment of warm-blooded animals, especially humans.

BACKGROUND OF THE INVENTION

The drug 4-[3,5-bis(2-hydroxyphenyl)-[1,2,4]triazol-1-yl]benzoic acid is an orally active iron chelator that is indicated in the treatment of iron overload in transfusion dependent anemias, in particular thalassemia major, thalassemia intermediate and in sickle cell disease to reduce iron-related morbidity and mortality. 4-[3,5-bis(2-hydroxyphenyl)-[1,2,4]triazol-1-yl]benzoic acid can also be used in the treatment of hemochromatosis. In general, the preparation of 4-[3,5-bis(2-hydroxyphenyl)-[1,2,4]triazol-1-yl]benzoic acid is known in the art. However, it is also known that different crystalline forms of the same drug may have substantial differences in certain pharmaceutically important properties. Therefore, there is a continuing need for new solid forms of 4-[3,5-bis(2-hydroxyphenyl)-[1,2,4]triazol-1-yl]benzoic acid and new methods of preparation.

SUMMARY OF THE INVENTION

In accordance with one aspect, the invention provides a crystalline form A of 4-[3,5-bis(2-hydroxyphenyl)-[1,2,4]triazol-1-yl]benzoic acid. Preferably, the crystalline form A of 4-[3,5-bis(2-hydroxyphenyl)-[1,2,4]triazol-1-yl]benzoic acid has an X-ray diffraction pattern with a peak at an angle of refraction 2 theta ($\theta$) of 10.0°, 10.5°, 14.1°, 16.6°, 23.1°, 25.1°, 25.7°, 26.2°±0.2° as depicted in FIG. 1. Preferably, the crystalline form A of 4-[3,5-bis(2-hydroxyphenyl)-[1,2,4]triazol-1-yl]benzoic acid has a Raman spectrum with significant bands 3083, 1623, 1609, 1517, 1458, 1352, 991 cm$^{-1}$±0.3 cm$^{-1}$ as depicted in FIG. 3.

In accordance with yet another aspect, the invention provides a composition that contains 4-[3,5-bis(2-hydroxyphenyl)-[1,2,4]triazol-1-yl]benzoic acid in a solid form, wherein at least 80% by weight of the solid 4-[3,5-bis(2-hydroxyphenyl)-[1,2,4]triazol-1-yl]benzoic acid is its crystalline form A having an X-ray diffraction pattern with a peak at an angle of refraction 2 $\theta$ of 10.0°, 10.5°, 14.1°, 16.6°, 23.1°, 25.1°, 25.7°, 26.2°±0.2° as depicted in FIG. 1. Various embodiments and variants are provided.

In accordance with yet another aspect, the invention provides a pharmaceutical composition that includes crystalline form A of 4-[3,5-bis(2-hydroxyphenyl)-[1,2,4]triazol-1-yl]benzoic acid and a pharmaceutically acceptable carrier or diluent. Preferably, the pharmaceutical composition is for oral administration.

In accordance with yet another aspect, the invention provides a process for making the crystalline form A of 4-[3,5-bis(2-hydroxyphenyl)-[1,2,4]triazol-1-yl]benzoic acid, the process including:
  (a) providing a solution of 4-[3,5-bis(2-hydroxyphenyl)-[1,2,4]triazol-1-yl]benzoic acid e.g. in amorphous form, in either a protic or an aprotic solvent;
  (b) cooling the solution to form the crystalline form A of 4-[3,5-bis(2-hydroxyphenyl)-[1,2,4]triazol-1-yl]benzoic acid; and
  (c) isolating the crystalline form A of 4-[3,5-bis(2-hydroxyphenyl)-[1,2,4]triazol-1-yl]benzoic acid. Various embodiments and variants are provided.

In accordance with one aspect, the invention provides a crystalline form B of 4-[3,5-bis(2-hydroxyphenyl)-[1,2,4]triazol-1-yl]benzoic acid. Preferably, the crystalline form B of 4-[3,5-bis(2-hydroxyphenyl)-[1,2,4]triazol-1-yl]benzoic acid has an X-ray diffraction pattern with a peak at an angle of refraction 2 theta ($\theta$) of 6.5°, 7.4°, 10.8°, 13.4°, 14.8°, 19.2°, 21.7°, 26.1°±0.2° as depicted in FIG. 4.

In accordance with yet another aspect, the invention provides a composition that contains 4-[3,5-bis(2-hydroxyphenyl)-[1,2,4]triazol-1-yl]benzoic acid in a solid form, wherein at least 80% by weight of the solid 4-[3,5-bis(2-hydroxyphenyl)-[1,2,4]triazol-1-yl]benzoic acid is its crystalline form B having an X-ray diffraction pattern with a peak at an angle of refraction 2 $\theta$ of 6.5°, 7.4°, 10.8°, 13.4°, 14.8°, 19.2°, 21.7°, 26.1°±0.2° as depicted in FIG. 4.

In accordance with yet another aspect, the invention provides a pharmaceutical composition that includes crystalline form B of 4-[3,5-bis(2-hydroxyphenyl)-[1,2,4]triazol-1-yl]benzoic acid and a pharmaceutically acceptable carrier or diluent. Preferably, the pharmaceutical composition is for oral administration.

One aspect of the present invention relates to a process for making the crystalline form B of 4-[3,5-bis(2-hydroxyphenyl)-[1,2,4]triazol-1-yl]benzoic acid, the process including:
  (a) heating the amorphous material above the glass transition temperature, e.g. above 95° C., e.g. above 95° C. or until a temperature equal to 105° C.,
  (b) starting the crystallisation by further heating at a temperature of, e.g. 150° C. until a temperature equal to about 190° C., e.g. equal to 190° C.,
  (c) isolating the crystals of crystalline form B of 4-[3,5-bis(2-hydroxyphenyl)-[1,2,4]triazol-1-yl]benzoic acid.

In a further embodiment the invention pertains to the amorphous form of 4-[3,5-bis(2-hydroxyphenyl)-[1,2,4]triazol-1-yl]benzoic acid and compositions containing the amorphous form of 4-[3,5-bis(2-hydroxyphenyl)-[1,2,4]triazol-1-yl]benzoic acid. Preferably, the amorphous form of 4-[3,5-bis(2-hydroxyphenyl)-[1,2,4]triazol-1-yl]benzoic acid has a Raman spectrum with significant bands 3079, 1624, 1608, 1519, 1496, 1472, 1460, 1362, 1316, 997, 991 cm$^{-1}$±3 cm$^{-1}$ as depicted in FIG. 7. Preferably, the amorphous form of 4-[3,5-bis(2-hydroxyphenyl)-[1,2,4]triazol-1-yl]benzoic acid shows on RAMAN spectroscopy bands at 1496, 1472, 1362, 1316 cm$^{-1}$±3 cm$^{-1}$ The invention pertains to a process for making the amorphous form of 4-[3,5-bis(2-hydroxyphenyl)-[1,2,4]triazol-1-yl]benzoic acid, said process comprises the following steps:
  (a) heating, e.g. the crystalline form of modification A or modification B, e.g. above its melting point of 261° C. for the crystalline form of modification A,
  (b) quenching to a temperature of about 20-25° C. or below rapidly to obtain the amorphous form.

The invention also pertains to an alternative process for making the amorphous form of 4-[3,5-bis(2-hydroxyphenyl)-[1,2,4]triazol-1-yl]benzoic acid, said process comprises the following steps:
- (a) dissolving the crystalline form of modification A or modification B of 4-[3,5-bis(2-hydroxyphenyl)-[1,2,4] triazol-1-yl]benzoic acid in a solvent, e.g. an aqueous solvent, e.g. water, or in a mixture of 50% organic solvent/50% aqueous medium, e.g. 50% water/50% methylbutylether, or 50% water/50% diethylether, or in a mixture of organic solvents, e.g. 50% 3 pentanone/50%methylbutylether, 50%1-octanol/50% toluene, or 50% dioxane/50% toluene, or 50%toluene/50% diisopropylether, or 50% n-hexane/50% acetonitrile
- (b) fast evaporation of the solvent, e.g. under a stream of nitrogen
- (c) isolating the amorphous solid The advantageous property of the amorphous form is its highest solubility, e.g. as compared to the crystalline form A or B.

Another aspect of the invention relates to a crystalline form $S_A$ of 4-[3,5-bis(2-hydroxyphenyl)-[1,2,4]triazol-1-yl]benzoic acid. Preferably, the crystalline form $S_A$ of 4-[3,5-bis(2-hydroxyphenyl)-[1,2,4]triazol-1-yl]benzoic acid has an X-ray diffraction pattern as depicted in FIG. 8.

In accordance with one aspect, the invention provides a crystalline form C of 4-[3,5-bis(2-hydroxyphenyl)-[1,2,4]triazol-1-yl]benzoic acid. Preferably, the crystalline form C of 4-[3,5-bis(2-hydroxyphenyl)-[1,2,4]triazol-1-yl]benzoic acid has an X-ray diffraction pattern with a peak at an angle of refraction 2 theta (θ) of 9.2°, 12.4°, 13.2°, 16.3°, 18.3°, 21.3°, 22.2°, 24.2°, 25.1°±0.2° as depicted in FIG. 9.

In accordance with another aspect, the invention provides a composition that contains 4-[3,5-bis(2-hydroxyphenyl)-[1,2,4]triazol-1-yl]benzoic acid in a solid form, wherein at least 80% by weight of the solid 4-[3,5-bis(2-hydroxyphenyl)-[1,2,4]triazol-1-yl]benzoic acid is its crystalline form C having an X-ray diffraction pattern with a peak at an angle of refraction 2 θ of 9.2°, 12.4°, 13.2°, 16.3°, 18.3°, 21.3°, 22.2°, 24.2°, 25.1°±0.2° as depicted in FIG. 9. Various embodiments and variants are provided.

In accordance with another aspect, the invention provides a pharmaceutical composition that includes crystalline form C of 4-[3,5-bis(2-hydroxyphenyl)-[1,2,4]triazol-1-yl]benzoic acid and a pharmaceutically acceptable carrier or diluent. Preferably, the pharmaceutical composition is for oral administration.

In accordance with another aspect, the invention provides a process for making the crystalline form C of 4-[3,5-bis(2-hydroxyphenyl)-[1,2,4]triazol-1-yl]benzoic acid, the process including:
- (a) 4-[3,5-bis(2-hydroxyphenyl)-[1,2,4]triazol-1-yl]benzoic acid is dissolved in THF/water/Ethanol, e.g. (2:4:4),
- (b) solution of step (b) is allowed to dry, e.g. by flushing with nitrogen at room temperature,
- (c) the dry precipitate of step (d) is resuspended with either a mixture V/V of a solvent 1, e.g. acetonitrile, methanol or dichloromethane and of solvent 2, e.g. n-hexane, toluene or cyclohexane,
- (d) the suspension or solution of step (c) is agitated using high-speed vortexer, e.g. at about 30° C., e.g. 30° C., e.g. for about 2 hours, e.g. 2 hours,
- (e) the solution of step (d) is evaporated, e.g. at room temperature, e.g. under a stream of nitrogen.
- (f) the modification C of step (f) is isolated.

In a further embodiment the invention pertains to the crystalline form C of 4-[3,5-bis(2-hydroxyphenyl)-[1,2,4]triazol-1-yl]benzoic acid and compositions containing the crystalline form C of 4-[3,5-bis(2-hydroxyphenyl)-[1,2,4]triazol-1-yl]benzoic acid. Preferably, the crystalline form C of 4-[3,5-bis(2-hydroxyphenyl)-[1,2,4]triazol-1-yl]benzoic acid has a Raman spectrum with significant bands 3066(w, broad), 2973 (w), 2940(w), 1601(st), 1530(w), 1517(m), 1467(m), 1414 (w), 1341(st), 1300(w), 1264(w), 1167(w), 1042(w), 986(m), 837(w), 781(w), 659(w), 413(w) and 166(w) cm$^{-1}$±3 cm$^{-1}$ as depicted in FIG. 10. Preferably, the crystalline form C of 4-[3,5-bis(2-hydroxyphenyl)-[1,2,4]triazol-1-yl]benzoic acid shows on RAMAN spectroscopy bands at 1601 and 1341 cm$^{-1}$±3 cm$^{-1}$ In accordance with another aspect, the invention provides a crystalline form D of 4-[3,5-bis(2-hydroxyphenyl)-[1,2,4]triazol-1-yl]benzoic acid. Preferably, the crystalline form D of 4-[3,5-bis(2-hydroxyphenyl)-[1,2,4]triazol-1-yl]benzoic acid has an X-ray diffraction pattern with a peak at an angle of refraction 2 theta (θ) of 7.0°, 9.4°, 10.6°, 11.3°, 13.9°, 15.0°, 20.4°, 21.4°±0.2° as depicted in FIG. 11.

In accordance with another aspect, the invention provides a composition that contains 4-[3,5-bis(2-hydroxyphenyl)-[1,2,4]triazol-1-yl]benzoic acid in a solid form, wherein at least 80% by weight of the solid 4-[3,5-bis(2-hydroxyphenyl)-[1,2,4]triazol-1-yl]benzoic acid is its crystalline form D having an X-ray diffraction pattern with a peak at an angle of refraction 2 θ of 7.0°, 9.4°, 10.6°, 11.3°, 13.9°, 15.0°, 20.4°, 21.4°±0.2° as depicted in FIG. 11.

In accordance with yet another aspect, the invention provides a pharmaceutical composition that includes crystalline form D of 4-[3,5-bis(2-hydroxyphenyl)-[1,2,4]triazol-1-yl]benzoic acid and a pharmaceutically acceptable carrier or diluent. Preferably, the pharmaceutical composition is for oral administration.

One aspect of the present invention relates to a process for making the crystalline form D of 4-[3,5-bis(2-hydroxyphenyl)-[1,2,4]triazol-1-yl]benzoic acid, the process including:
- (a) suspending the modification A material in a solvent, e.g. a mixture of diethylamine/cyclohexane v/v (1/1),
- (b) mixing the suspension of step (a), e.g. at 30° C. e.g. for 2 hours,
- (c) filtering the mixture of step (b), e.g. on a 0.2 mm filter, e.g. with regular cellulose membrane,
- (d) evaporating the solution of step (c), e.g. under stream of $N_2$,
- (e) isolating the crystals of crystalline form D of 4-[3,5-bis(2-hydroxyphenyl)-[1,2,4]triazol-1-yl]benzoic acid.

In a further embodiment the invention pertains to the crystalline form D of 4-[3,5-bis(2-hydroxyphenyl)-[1,2,4]triazol-1-yl]benzoic acid and compositions containing the crystalline form D of 4-[3,5-bis(2-hydroxyphenyl)-[1,2,4]triazol-1-yl]benzoic acid. Preferably, the form D of 4-[3,5-bis(2-hydroxyphenyl)-[1,2,4]triazol-1-yl]benzoic acid has a Raman spectrum with significant bands 3071 (w, broad), 2973 (w, broad), 2940 (w, broad), 2887 (w, broad), 2852 (w, broad), 1604 (st), 1521 (m), 1483 (w, broad), 1462 (w, broad), 1385 (w, broad), 1346 (st), 1266 (w), 1158 (w), 1137 (w), 1034 (w), 984 (w), 660 (w), 414 (w) and 115 (w) cm$^{-1}$ as depicted in FIG. 12. Preferably, the crystalline form D of 4-[43,5-bis(2-hydroxyphenyl)-[1,2,4]triazol-1-yl]benzoic acid shows on RAMAN spectroscopy bands at 1521 and 1483 cm$^{-1}$±3 cm$^{-1}$.

Another aspect of the invention relates to a crystalline form $S_B$ of 4-[3,5-bis(2-hydroxyphenyl)-[1,2,4]triazol-1-yl]benzoic acid. Preferably, the crystalline form $S_B$ of 4-[3,5-bis(2-hydroxyphenyl)-[1,2,4]triazol-1-yl]benzoic acid has an X-ray diffraction pattern as depicted in FIG. 13.

In accordance with one aspect, the invention provides a crystalline form $S_B$ of 4-[3,5-bis(2-hydroxyphenyl)-[1,2,4]triazol-1-yl]benzoic acid. Preferably, the crystalline form $S_B$ of 4-[3,5-bis(2-hydroxyphenyl)-[1,2,4]triazol-1-yl]benzoic acid has an X-ray diffraction pattern with a peak at an angle of refraction 2 theta (θ) of 9.4°, 10.0°, 11.3°, 12.8°, 15.0°, 16.1°, 22.1°, 24.3°±0.2° as depicted in FIG. 13.

In accordance with yet another aspect, the invention provides a composition that contains 4-[3,5-bis(2-hydroxyphenyl)-[1,2,4]triazol-1-yl]benzoic acid in a solid form, wherein at least 80% by weight of the solid 4-[3,5-bis(2-hydroxyphenyl)-[1,2,4]triazol-1-yl]benzoic acid is its crystalline form $S_B$ having an X-ray diffraction pattern with a peak at an angle of refraction 2 θ of 9.4°, 10.0°, 11.3°, 12.8°, 15.0°, 16.1°, 22.1°, 24.3°±0.2° as depicted in FIG. 13.

In accordance with yet another aspect, the invention provides a pharmaceutical composition that includes crystalline form $S_B$ of 4-[3,5-bis(2-hydroxyphenyl)-[1,2,4]triazol-1-yl]benzoic acid and a pharmaceutically acceptable carrier or diluent. Preferably, the pharmaceutical composition is for oral administration.

BRIEF DESCRIPTION OF THE DRAWINGS

FIG. 9 shows the X-ray powder diffraction diagram of crystalline form C of 4-[3,5-bis(2-hydroxyphenyl)-[1,2,4]triazol-1-yl]benzoic acid.

FIG. 10 shows the Raman spectrum crystalline form C of 4-[3,5-bis(2-hydroxyphenyl)-[1,2,4]triazol-1-yl]benzoic acid.

FIG. 11 shows the X-ray powder diffraction diagram of crystalline form D of 4-[3,5-bis(2-hydroxyphenyl)-[1,2,4]triazol-1-yl]benzoic acid.

FIG. 12 shows the Raman spectrum crystalline form D of 4-[3,5-bis(2-hydroxyphenyl)-[1,2,4]triazol-1-yl]benzoic acid.

FIG. 13 shows the X-ray powder diffraction diagram of solvate form $S_B$ 4-[3,5-bis(2-hydroxyphenyl)-[1,2,4]triazol-1-yl]benzoic acid.

DETAILED DESCRIPTION OF THE INVENTION

Figure 1:
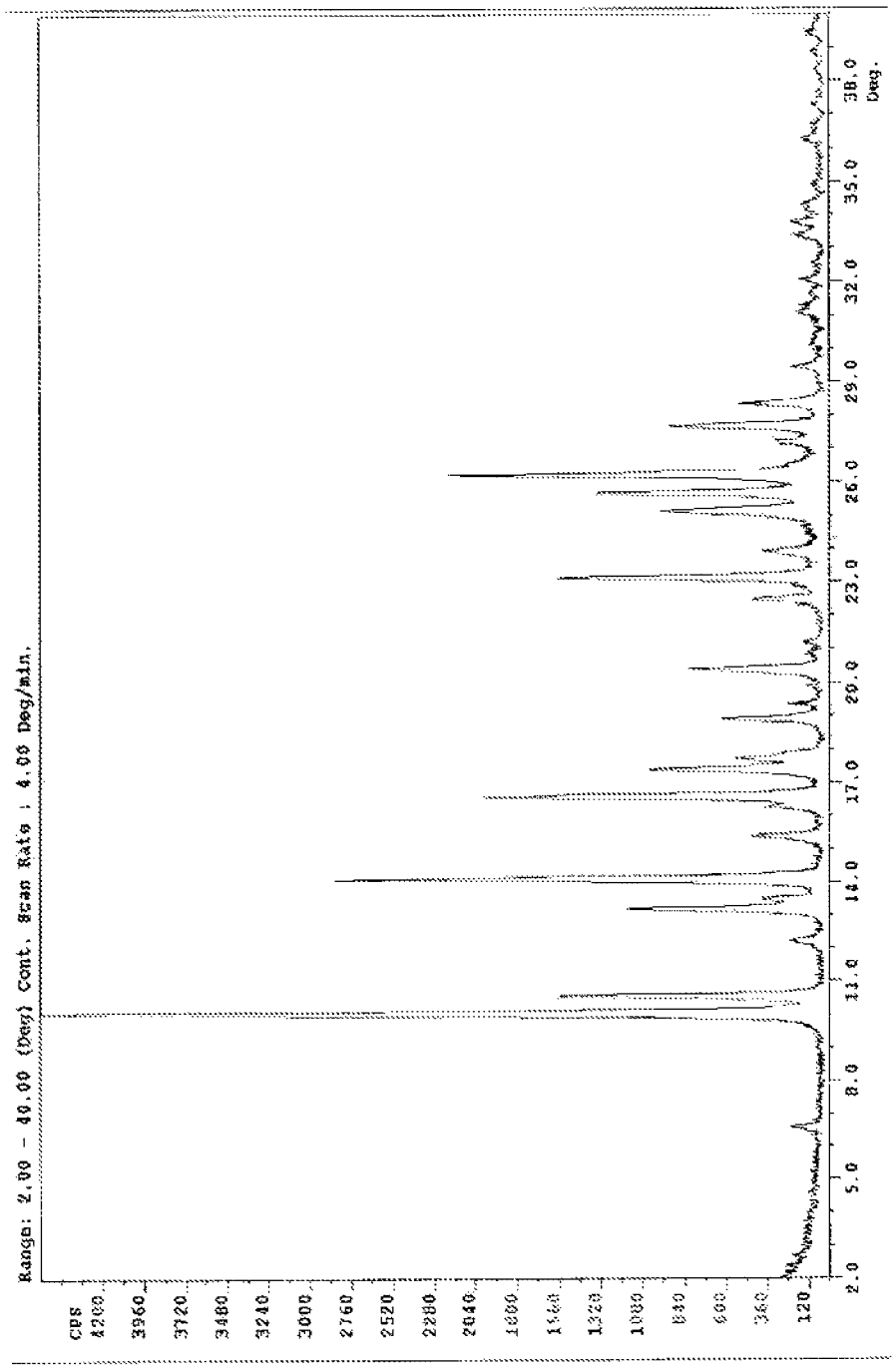
FIG. 1 shows the X-ray powder diffraction diagram of crystalline form A of 4-[3,5-bis(2-hydroxyphenyl)-[1,2,4]triazol-1-yl]benzoic acid.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

For the purposes of the present invention, the following terms are defined below. The crystalline compound, designated herein as "crystalline form A" and referred to hereinafter as crystalline form A of 4-[3,5-bis(2-hydroxyphenyl)-[1,2,4]triazol-1-yl]benzoic acid, is a new crystalline polymorph of 4-[3,5-bis(2-hydroxyphenyl)-[1,2,4]triazol-1-yl]benzoic acid different from known polymorphs. It is characterized via X-ray powder diffraction and DSC. It is further described below.

The crystalline compound, designated herein as "crystalline form B" and referred to hereinafter as crystalline form B of 4-[3,5-bis(2-hydroxyphenyl)-[1,2,4]triazol-1-yl]benzoic acid, is a new crystalline polymorph of 4-[3,5-bis(2-hydroxyphenyl)-[1,2,4]triazol-1-yl]benzoic acid different from known polymorphs. It is characterized via X-ray powder diffraction and DSC. It is further described below.

4-[3,5-bis(2-hydroxyphenyl)-[1,2,4]triazol-1-yl]benzoic acid can also be in the amorphous form.

For the purposes of the present invention, the following terms are defined below. The crystalline compound, designated herein as "crystalline form C" and referred to hereinafter as crystalline form C of 4-[3,5-bis(2-hydroxyphenyl)-[1,2,4]triazol-1-yl]benzoic acid, is a new crystalline polymorph of 4-[3,5-bis(2-hydroxyphenyl)-[1,2,4]triazol-1-yl]benzoic acid different from known polymorphs. It is characterized via X-ray powder diffraction. It is further described below.

The crystalline compound, designated herein as "crystalline form D" and referred to hereinafter as crystalline form D of 4-[3,5-bis(2-hydroxyphenyl)-[1,2,4]triazol-1-yl]benzoic acid, is a new crystalline polymorph of 4-[3,5-bis(2-hydroxyphenyl)-[1,2,4]triazol-1-yl]benzoic acid different from known polymorphs. It is characterized via X-ray powder diffraction. It is further described below.

The crystalline compound, designated herein as "crystalline form $S_B$" and referred to hereinafter as crystalline form $S_B$ of 4-[3,5-bis(2-hydroxyphenyl)-[1,2,4]triazol-1-yl]benzoic acid, is a new crystalline polymorph of 4-[3,5-bis(2-hydroxyphenyl)-[1,2,4]triazol-1-yl]benzoic acid different from known polymorphs. It is characterized via X-ray powder diffraction. It is further described below.

"Pharmaceutically acceptable" means that which is useful in preparing a pharmaceutical composition that is generally non-toxic and is not biologically undesirable and includes that which is acceptable for veterinary use and/or human pharmaceutical use.

The term "composition" includes, but is not limited to, a powder, a solution, a suspension, a gel, an ointment, an emulsion and/or mixtures thereof. The term composition is intended to encompass a product containing the specified ingredients in the specified amounts, as well as any product, which results, directly or indirectly, from combination of the specified ingredients in the specified amounts. A "composition" may contain a single compound or a mixture of compounds. A "compound" is a chemical substance that includes molecules of the same chemical structure.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the active ingredient, additional active ingredient(s) and pharmaceutically acceptable excipients.

The term "excipient" means a component of a pharmaceutical product that is not the active ingredient, such as filler, diluent and carrier. The excipients that are useful in preparing a pharmaceutical composition are preferably generally safe, non-toxic and neither biologically nor otherwise undesirable, and are acceptable for veterinary use, as well as human pharmaceutical use. "A pharmaceutically acceptable excipient", as used in the specification and claims, includes both one and more than one such excipient.

"Therapeutically effective amount" means the amount of a compound that, when administered for treating or preventing a disease, is sufficient to effect such treatment or prevention for the disease. The "therapeutically effective amount" will vary depending on the compound, the disease and its severity and the age, weight, etc., of the patient to be treated.

When referring to a chemical reaction, the terms "treating", "contacting" and "reacting" are used interchangeably herein and refer to adding or mixing two or more reagents under appropriate conditions to produce the indicated and/or desired product. It should be appreciated that the reaction which produces the indicated and/or desired product may not necessarily result directly from the combination of two reagents which were initially added, i.e., there may be one or more intermediates which are produced in the mixture which ultimately leads to the formation of the indicated and/or desired product.

The term "substantially free of" in reference to a composition, as used herein, means that the substance form which the composition is free of cannot be detected by methods known to those skilled in the art.

The term "essentially pure" is understood in the context of the present invention to mean especially that at least 90%, preferably at least 95% by weight of the crystals of an acid addition salt of formula (I) are present in the crystal form according to the invention.

In the context with stating that, e.g. the A, B, C or D-crystal form of 4-[3,5-bis(2-hydroxyphenyl)-[1,2,4]triazol-1-yl]benzoic acid exhibits an X-ray diffraction diagram essentially as in FIG. 1, 4, 9 or 11 respectively, the term "essentially" means that at least the major lines of the diagram depicted in FIG. 1, 4, 9 or 11 respectively, i.e. those having a relative line intensity of more than 20%, especially more than 30%, as compared to the most intense line in the diagram, have to be present.

Figure 8:
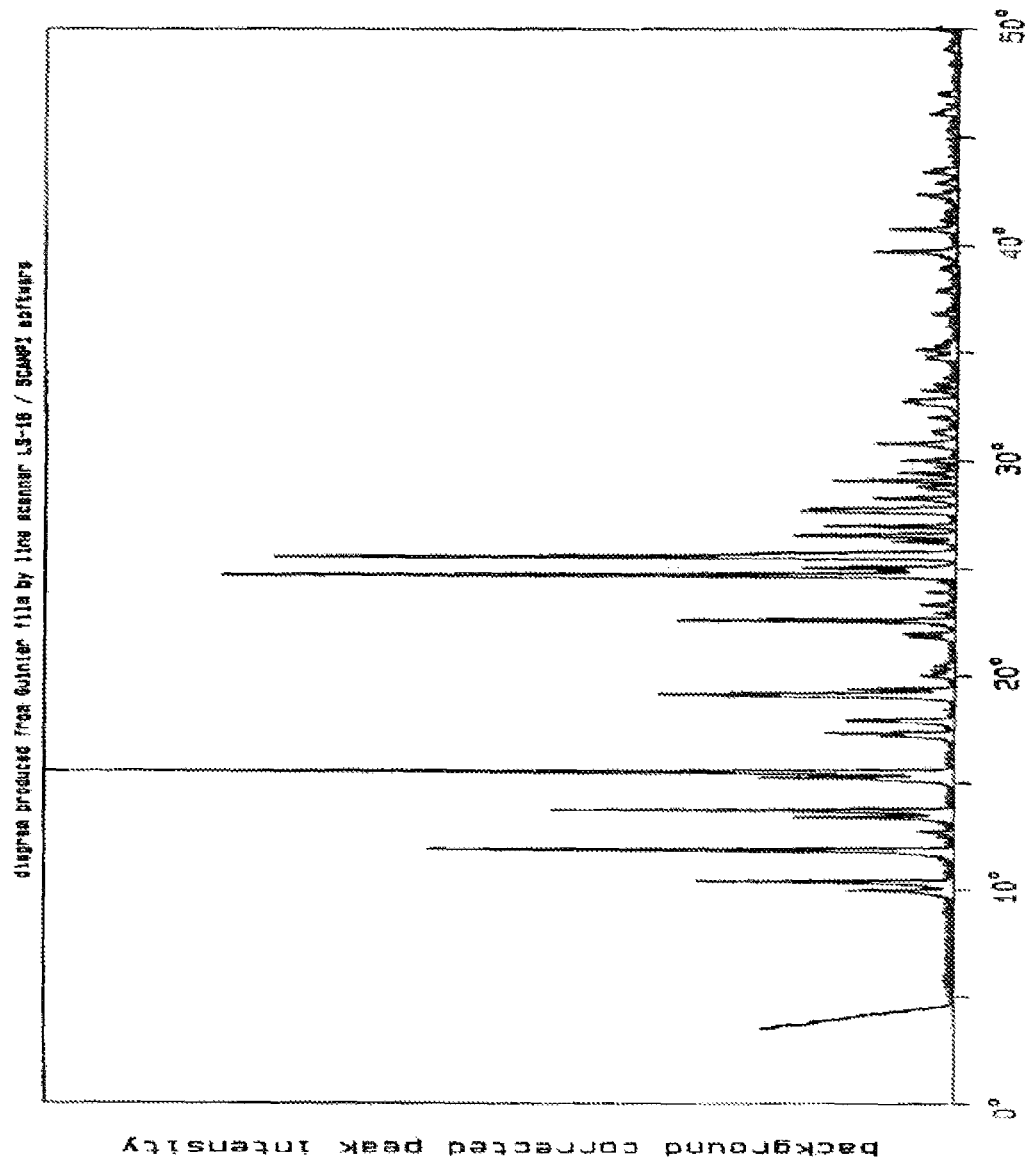
FIG. 8 shows the X-ray powder diffraction diagram of solvate form $S_A$ 4-[3,5-bis(2-hydroxyphenyl)-[1,2,4]triazol-1-yl]benzoic acid.

In the context with stating that, e.g. the $S_A$ or $S_B$-crystal form of 4-[3,5-bis(2-hydroxyphenyl)-[1,2,4]triazol-1-yl]benzoic acid exhibits an X-ray diffraction diagram essentially as in FIG. 8 or 13 respectively, the term "essentially" means that at least the major lines of the diagram depicted in FIG. 8 or 13 respectively, i.e. those having a relative line intensity of more than 20%, especially more than 30%, as compared to the most intense line in the diagram, have to be present.

4-[3,5-bis(2-hydroxyphenyl)-[1,2,4]triazol-1-yl]benzoic acid has the following chemical structure:

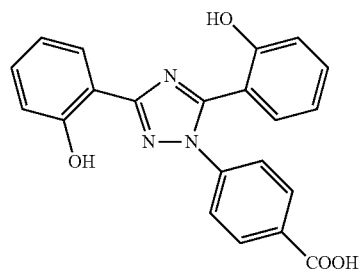 [SMILES: O=C(O)c1ccc(-n2nc(-c3ccccc3O)nc2-c2ccccc2O)cc1]

4-[3,5-bis(2-hydroxyphenyl)-[1,2,4]triazol-1-yl]benzoic acid is described in example 5 of the granted EP 0911418, its manufacturing process is also described in EP 0914118.

The invention relates to a crystalline form A of 4-[3,5-bis(2-hydroxyphenyl)-[1,2,4]triazol-1-yl]benzoic acid, to a crystalline form B of 4-[3,5-bis(2-hydroxyphenyl)-[1,2,4]triazol-1-yl]benzoic acid, to a crystalline form C of 4-[3,5-bis(2-hydroxyphenyl)-[1,2,4]triazol-1-yl]benzoic acid, to a crystalline form D of 4-[3,5-bis(2-hydroxyphenyl)-[1,2,4]triazol-1-yl]benzoic acid, to a solvate form $S_A$ of 4-[3,5-bis(2-hydroxyphenyl)-[1,2,4]triazol-1-yl]benzoic acid, to a solvate form $S_B$ of 4-[3,5-bis(2-hydroxyphenyl)-[1,2,4]triazol-1-yl]benzoic acid and to an amorphous form of 4-[3,5-bis(2-hydroxyphenyl)-[1,2,4]triazol-1-yl]benzoic acid.

Different solid forms of the same drug may exhibit different properties, including characteristics that have functional implications with respect to their use as drug may have substantial differences in such pharmaceutically important properties as dissolution rates and bioavailability. Likewise, different polymorphs may have different processing properties, such as hydroscopisity, flowability and the like, which could affect their suitability as active pharmaceuticals for commercial production.

X-ray powder diffraction patterns was measured on a Scintag X1 with CuK alpha radiation source, e.g. using a wavelength of 0.15406 nm. The X-ray diffraction pattern depicted in FIG. 1 is summarized in Table 1.

TABLE 1

Powder X-Ray Diffraction Peaks for the Form A Crystal Modification of 4-[3,5-bis(2-hydroxyphenyl)-[1,2,4]triazol-1-yl]benzoic acid

| ° deg 2 θ | d-space/Å | Relative intensity |
| --- | --- | --- |
| 10.0 | 8.20 | medium |
| 10.5 | 8.45 | medium |
| 14.1 | 6.32 | medium |
| 16.6 | 5.39 | strong |
| 23.1 | 3.93 | medium |
| 25.1 | 3.63 | medium |
| 25.7 | 3.55 | medium |
| 26.2 | 3.49 | low |

It should be kept in mind that slight variations in observed 2θ angles or d-spacing values are expected based on the specific diffractometer employed, the analyst and the sample preparation technique. More variation is expected for the relative peak intensities.

Identification of the exact crystalline form of a compound should be based primarily on observed 2 θ angles with lesser importance attributed to relative peak intensities. Some margin of error is present in each of the 2θ angle assignments reported herein. The assigned margin of error, in a preferred variant, the crystalline form A of 4-[3,5-bis(2-hydroxyphenyl)-[1,2,4]triazol-1-yl]benzoic acid is approximately ±0.2° for each of the peak assignments.

Figure 2:
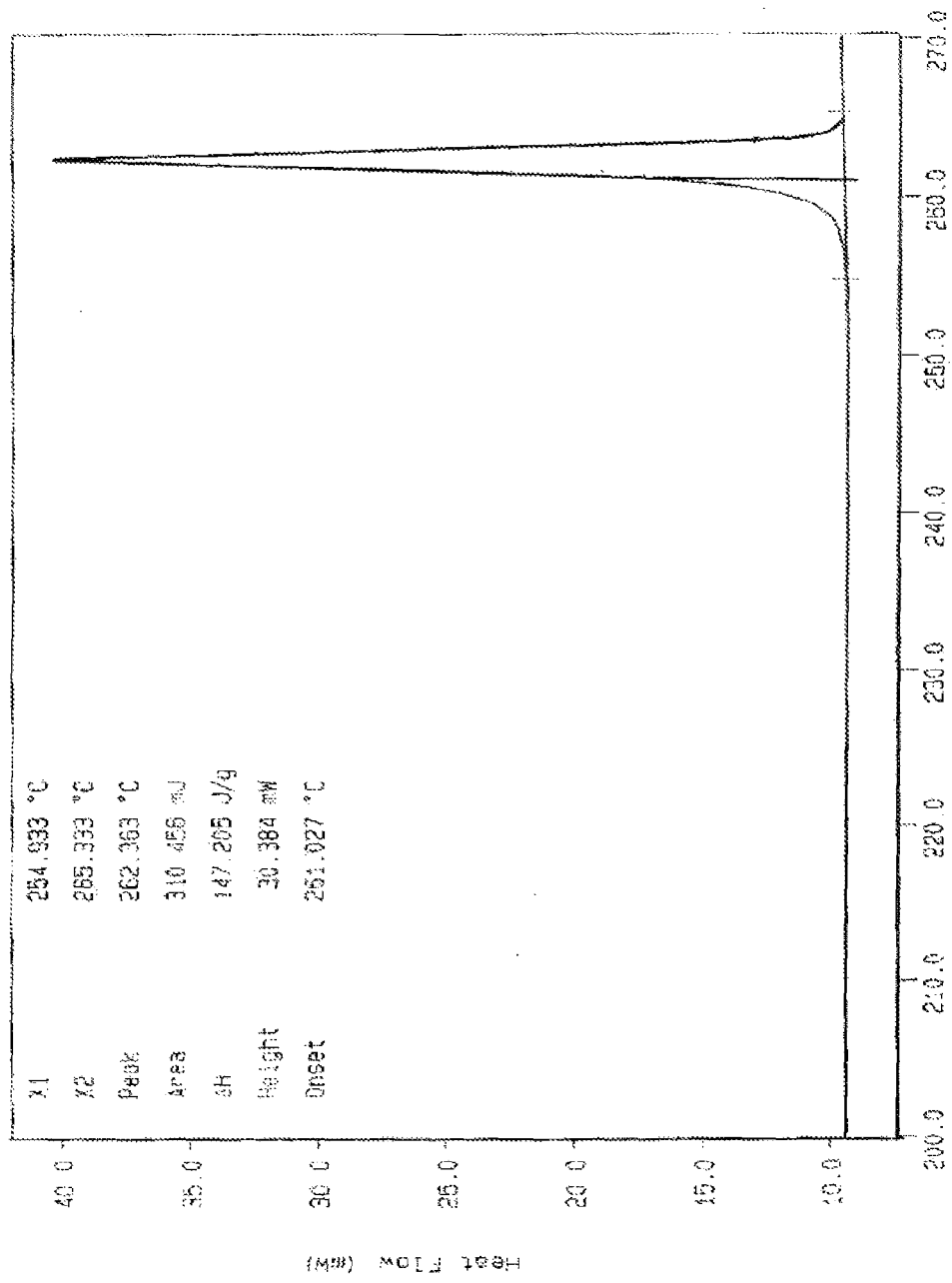
FIG. 2 shows the DSC curve of crystalline form A of 4-[3,5-bis(2-hydroxyphenyl)-[1,2,4]triazol-1-yl]benzoic acid.
Figure 3:
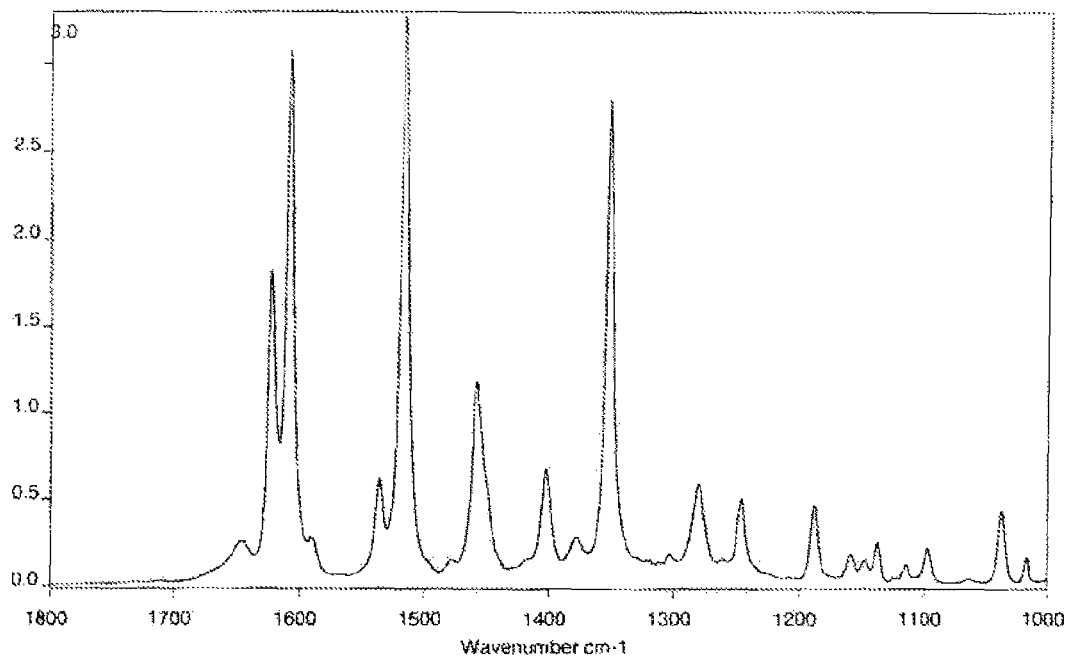
FIG. 3 shows the Raman spectrum crystalline form A of 4-[3,5-bis(2-hydroxyphenyl)-[1,2,4]triazol-1-yl]benzoic acid.
Figure 3:
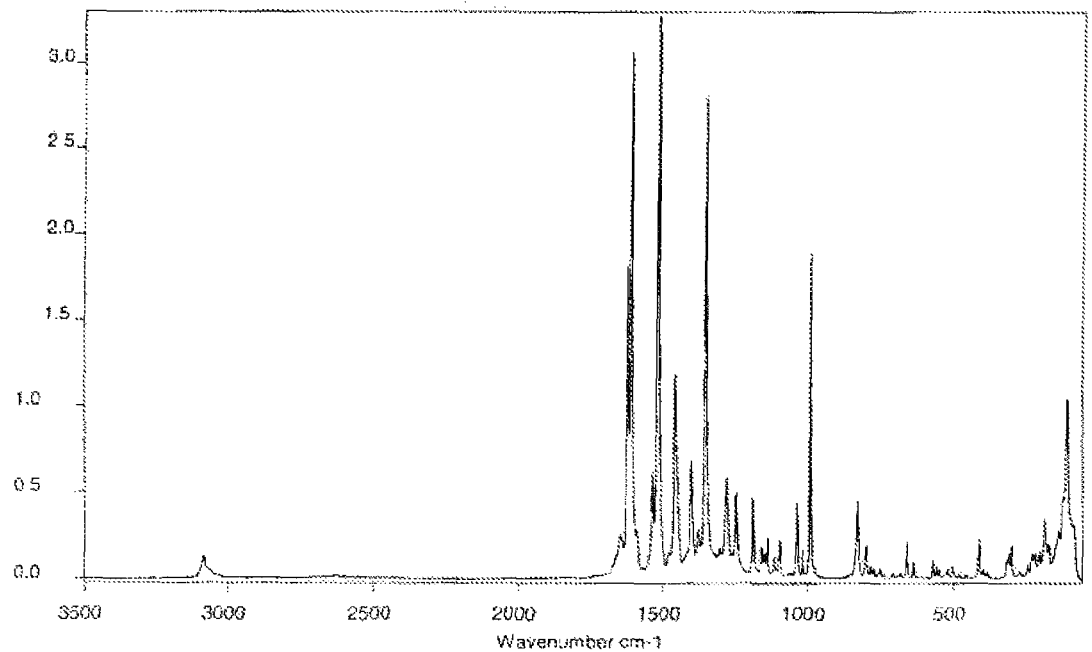

The crystalline form A of 4-[3,5-bis(2-hydroxyphenyl)-[1,2,4]triazol-1-yl]benzoic acid may be also characterized by Differential Scanning Calorimeter (DSC). The crystalline form A exhibits a characteristic pattern in Differential Scanning calorimeter (DSC) analysis as depicted in FIG. 2. DSC analysis was measured on a Perkin Elmer DSC7 at a heating rate of 10 K/min. The crystalline form A of 4-[3,5-bis(2-hydroxyphenyl)-[1,2,4]triazol-1-yl]benzoic acid has a characteristic peak at about 261° C., e.g. at 261° C. Some margin of error is present in each of the characteristic peak reported herein. The assigned margin of error is approximately +/−2K, but can be larger, e.g. in particular lower if impurities are present.

One or more of physical properties and/or spectroscopic properties can be the basis for characterizing the crystal or polymorphic forms of 4-[3,5-bis(2-hydroxyphenyl)-[1,2,4]triazol-1-yl]benzoic acid.

The invention also provides a composition containing solid 4-[3,5-bis(2-hydroxyphenyl)-[1,2,4]triazol-1-yl]benzoic acid, which is at least 80%, by total weight of the solid 4-[3,5-bis(2-hydroxyphenyl)-[1,2,4]triazol-1-yl]benzoic acid in the composition, its crystalline form A. The preferred form of this composition is solid 4-[3,5-bis(2-hydroxyphenyl)-[1,2,4]triazol-1-yl]benzoic acid powder suitable for use as active ingredient in formulating pharmaceutical products. The remainder of the solid 4-[3,5-bis(2-hydroxyphenyl)-[1,2,4]triazol-1-yl]benzoic acid in the composition, i.e., 20% or less of the total weight of 4-[3,5-bis(2-hydroxyphenyl)-[1,2,4]triazol-1-yl]benzoic acid may be, e.g., other crystalline forms of 4-[3,5-bis(2-hydroxyphenyl)-[1,2,4]triazol-1-yl] benzoic acid. In one specific embodiment, the composition contains at least 90% of the crystalline form A of 4-[3,5-bis(2-hydroxyphenyl)-[1,2,4]triazol-1-yl]benzoic acid with respect to the total weight of the solid 4-[3,5-bis(2-hydroxyphenyl)-[1,2,4]triazol-1-yl]benzoic acid in the composition. In another specific embodiment, the composition contains at least 95% of the crystalline form A with respect to total weight of the solid 4-[3,5-bis(2-hydroxyphenyl)-[1,2,4]triazol-1-yl]benzoic acid in the composition.

A process for the preparation of crystalline form A of 4-[3,5-bis(2-hydroxyphenyl)-[1,2,4]triazol-1-yl]benzoic acid is also provided. The process involves:
(a) providing a solution 4-[3,5-bis(2-hydroxyphenyl)-[1,2,4]triazol-1-yl]benzoic acid in either a protic or aprotic solvent, e.g. using the amorphous form of 4-[3,5-bis(2-hydroxyphenyl)-[1,2,4]triazol-1-yl]benzoic acid;
(b) cooling the solution to form crystalline form A of 4-[3,5-bis(2-hydroxyphenyl)-[1,2,4]triazol-1-yl]benzoic acid; and
(c) isolating the crystalline form A of 4-[3,5-bis(2-hydroxyphenyl)-[1,2,4]triazol-1-yl]benzoic acid.

Non-limiting examples of the protic or aprotic solvents are the following: THF (tetrahydrofuran)/Ethanol; Toluene/THF; Methanol/THF; Formic acid/ethanol; Water; HXF.

In one embodiment, 4-[3,5-bis(2-hydroxyphenyl)-[1,2,4]triazol-1-yl]benzoic acid is dissolved in THF/Ethanol and heated to a temperature to obtain the crystalline form A of 4-[3,5-bis(2-hydroxyphenyl)-[1,2,4]triazol-1-yl]benzoic acid. This process is highly-reproducible and the resulting crystalline product has good filtration.

The above conditions on the selective preparation of the individual crystal forms are not conclusive. In general, e.g., it is possible to vary parameters such as the weight ratio of the compound of formula (I) to the solvent and anti-solvent.

Figure 4:
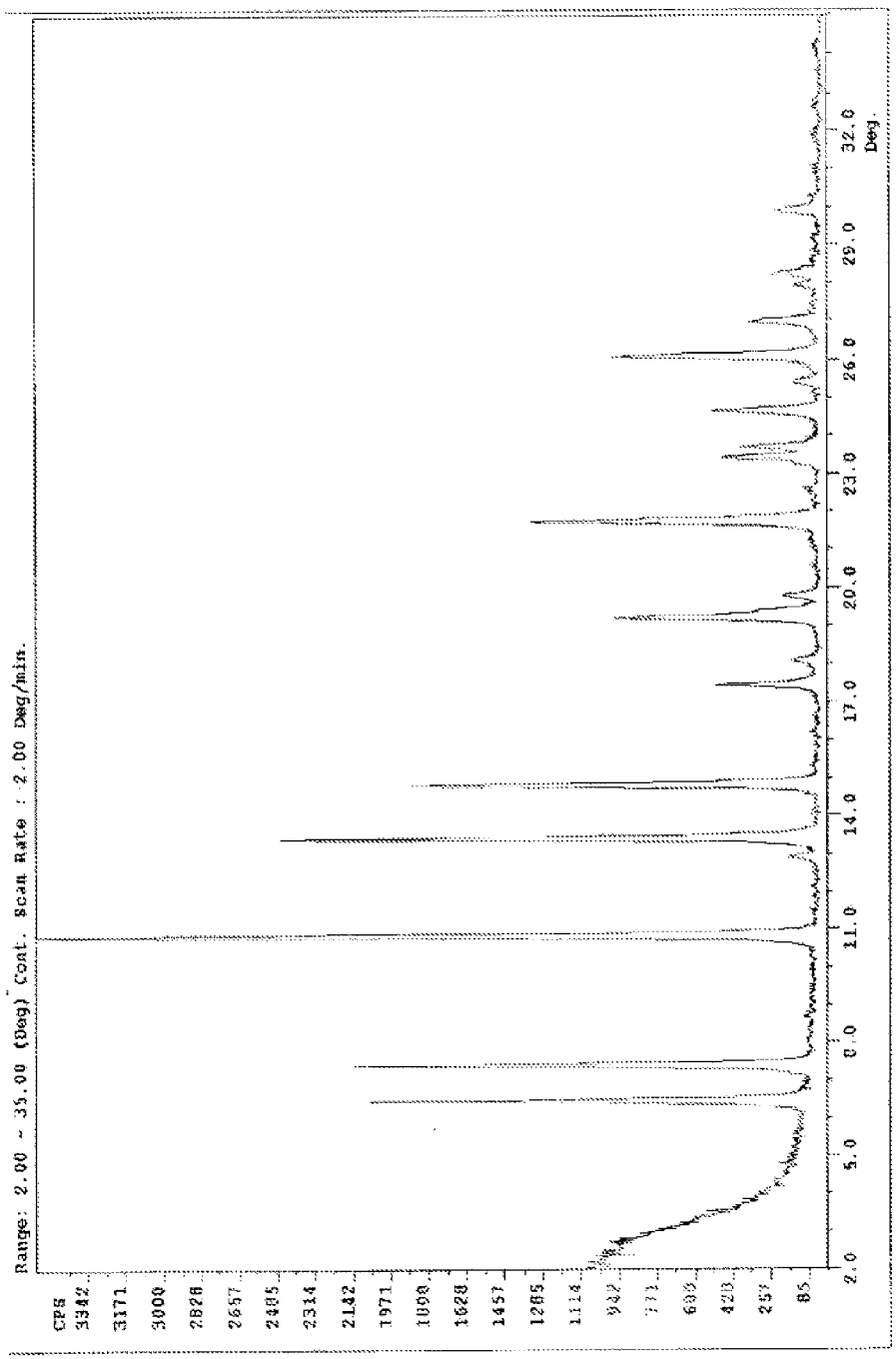
FIG. 4 shows the X-ray powder diffraction diagram of crystalline form B of 4-[3,5-bis(2-hydroxyphenyl)-[1,2,4]triazol-1-yl]benzoic acid.
Figure 5:
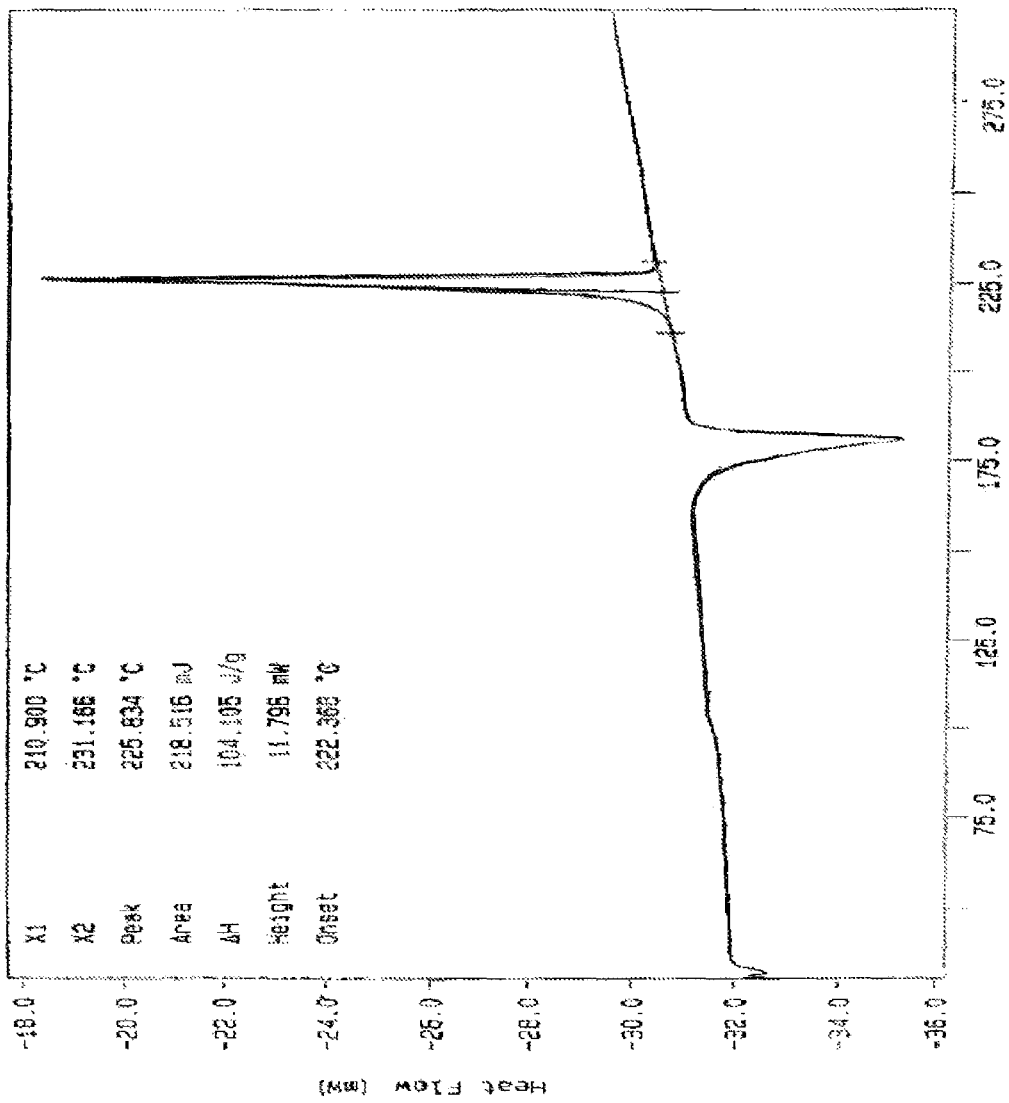
FIG. 5 shows the DSC curve of crystalline form B of 4-[3,5-bis(2-hydroxyphenyl)-[1,2,4]triazol-1-yl]benzoic acid.
Figure 6:
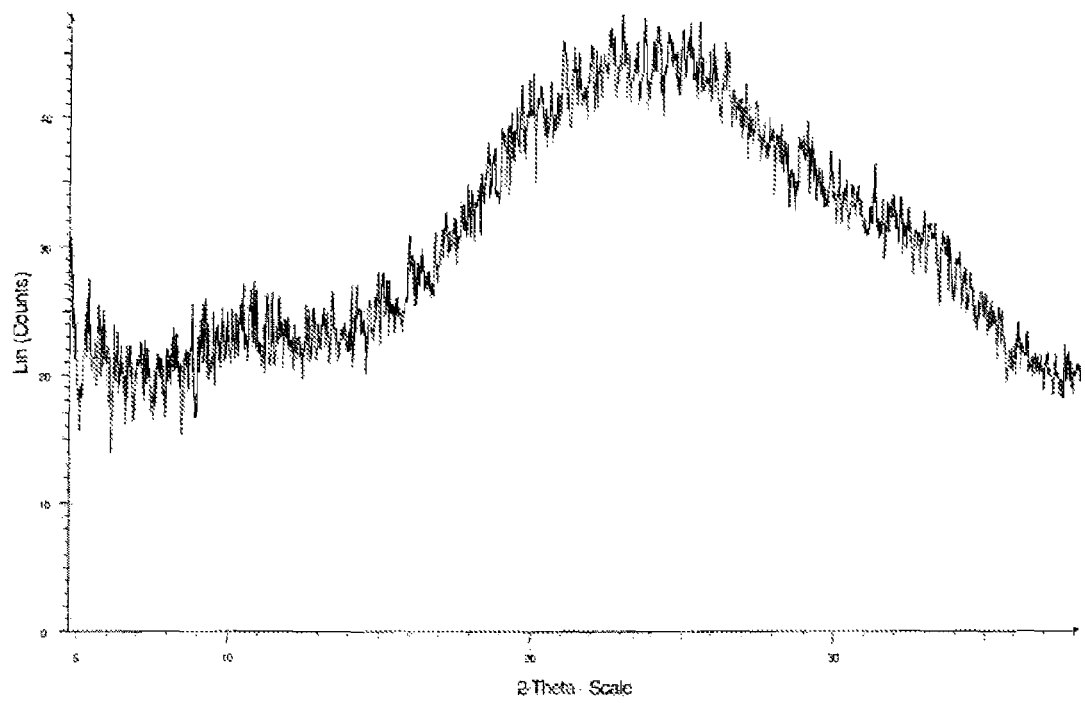
FIG. 6 shows the X-ray powder diffraction diagram of amorphous 4-[3,5-bis(2-hydroxyphenyl)-[1,2,4]triazol-1-yl]benzoic acid.
Figure 7:
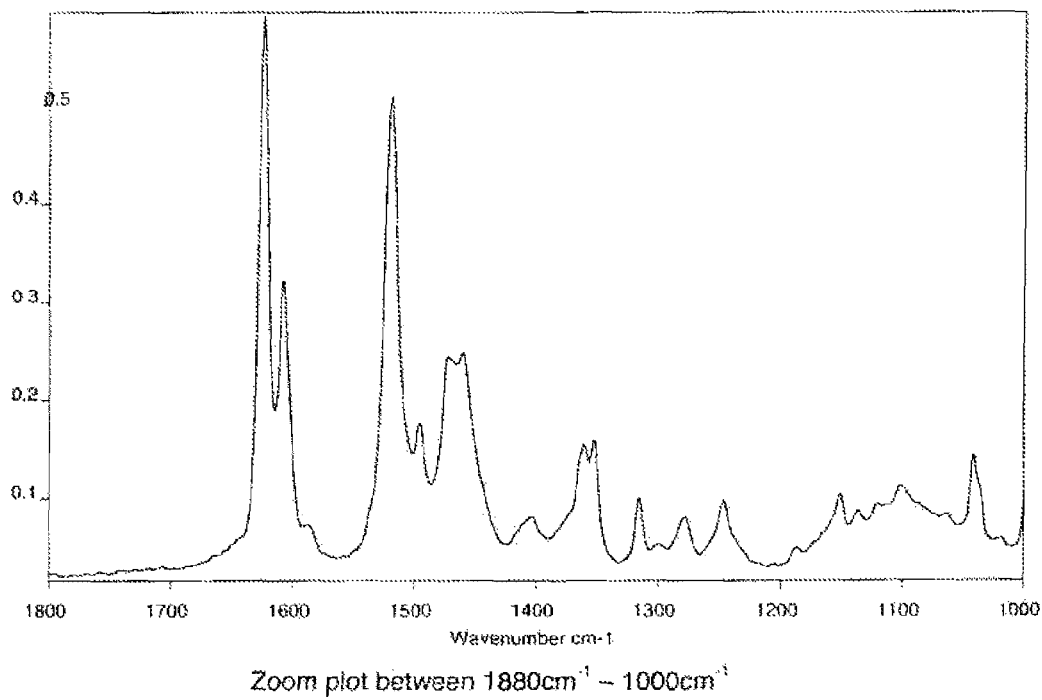
FIG. 7 shows the Raman spectrum of amorphous 4-[3,5-bis(2-hydroxyphenyl)-[1,2,4]triazol-1-yl]benzoic acid.
Figure 7:
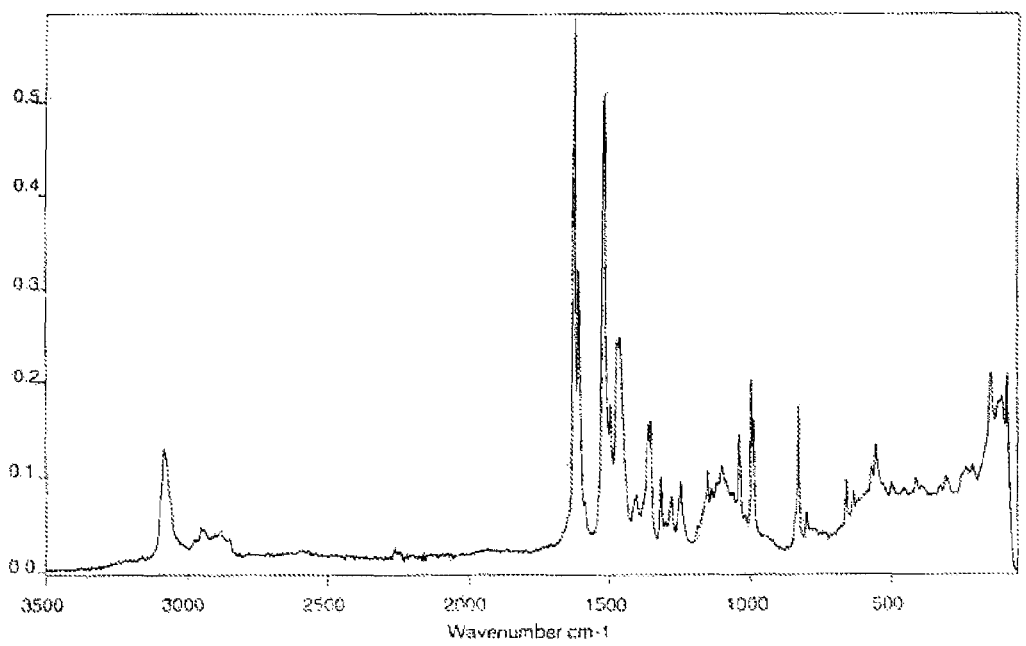

X-ray powder diffraction patterns was measured on a Scintag X1 with CuK alpha radiation source. The X-ray diffraction pattern depicted in FIG. 4 is summarized in Table 2.

TABLE 2

Powder X-Ray Diffraction Peaks for the Form B Crystal Modification of 4-[3,5-bis(2-hydroxyphenyl)-[1,2,4]triazol-1-yl]benzoic acid

| ° deg 2 θ | d-space/Å | Relative intensity |
|---|---|---|
| 6.5 | 13.67 | medium |
| 7.4 | 11.93 | medium |
| 10.8 | 8.16 | strong |
| 13.4 | 6.60 | medium |
| 14.8 | 5.97 | medium |
| 19.2 | 4.61 | low |
| 21.7 | 4.08 | medium |
| 26.1 | 3.41 | low |

It should be kept in mind that slight variations in observed 2 θ angles or d-spacing values are expected based on the specific diffractometer employed, the analyst and the sample preparation technique. More variation is expected for the relative peak intensities. Identification of the exact crystalline form of a compound should be based primarily on observed 2 θ angles with lesser importance attributed to relative peak intensities.

Some margin of error is present in each of the 2 θ angle assignments reported herein. The assigned margin of error, in a preferred variant, the crystalline form B of 4-[3,5-bis(2-hydroxyphenyl)-[1,2,4]triazol-1-yl]benzoic acid is approximately ±0.2° for each of the peak assignments.

The crystalline form B of 4-[3,5-bis(2-hydroxyphenyl)-[1,2,4]triazol-1-yl]benzoic acid may be also characterized by Differential Scanning calorimeter (DSC). The crystalline form B exhibits a characteristic pattern in Differential Scanning calorimeter (DSC) analysis as depicted in FIG. 4. DSC analysis was measured on a Perkin Elmer DSC7. The crystalline form B of 4-[3,5-bis(2-hydroxyphenyl)-[1,2,4]triazol-1-yl]benzoic acid has a characteristic peak at 226° C. Some margin of error is present in each of the characteristic peak reported herein. The assigned margin of error is +/−2K, but can be larger, e.g. in particular lower if purities are present.

One or more of physical properties and/or spectroscopic properties can be the basis for characterizing the crystal or polymorphic forms of 4-[3,5-bis(2-hydroxyphenyl)-[1,2,4]triazol-1-yl]benzoic acid.

The invention also provides a composition containing solid 4-[3,5-bis(2-hydroxyphenyl)-[1,2,4]triazol-1-yl]benzoic acid, which is at least 80%, by total weight of the solid 4-[3,5-bis(2-hydroxyphenyl)-[1,2,4]triazol-1-yl]benzoic acid in the composition, its crystalline form B. The preferred form of this composition is solid 4-[3,5-bis(2-hydroxyphenyl)-[1,2,4]triazol-1-yl]benzoic acid powder suitable for use as active ingredient in formulating pharmaceutical products. The remainder of the solid 4-[3,5-bis(2-hydroxyphenyl)-[1,2,4]triazol-1-yl]benzoic acid in the composition, i.e., 20% or less of the total weight of 4-[3,5-bis(2-hydroxyphenyl)-[1,2,4]triazol-1-yl]benzoic acid may be, e.g., other crystalline forms of 4-[3,5-bis(2-hydroxyphenyl)-[1,2,4]triazol-1-yl] benzoic acid. In one specific embodiment, the composition contains at least 90% of the crystalline form B of 4-[3,5-bis(2-hydroxyphenyl)-[1,2,4]triazol-1-yl]benzoic acid with respect to the total weight of the solid 4-[3,5-bis(2-hydroxyphenyl)-[1,2,4]triazol-1-yl]benzoic acid in the composition.

In another specific embodiment, the composition contains at least 95% of the crystalline form B with respect to total weight of the solid 4-[3,5-bis(2-hydroxyphenyl)-[1,2,4]triazol-1-yl]benzoic acid in the composition.

A process for the preparation of crystalline form B of 4-[3,5-bis(2-hydroxyphenyl)-[1,2,4]triazol-1-yl]benzoic acid involves the following steps:
  (a) heating the crystalline form A of 4-[3,5-bis(2-hydroxyphenyl)-[1,2,4]triazol-1-yl]benzoic acid to above its melting point of about 261° C.,
  (b) cooling the melt of 4-[3,5-bis(2-hydroxyphenyl)-[1,2,4]triazol-1-yl]benzoic of step (a) to about room temperature or below to obtain the amorphous form,
  (c) recrystallization of the amorphous form of 4-[3,5-bis(2-hydroxyphenyl)-[1,2,4]triazol-1-yl] into crystalline form B upon heating to a temperature above 95° C., preferably to above 190° C.,
  (d) crystalline form B of 4-[3,5-bis(2-hydroxyphenyl)-[1,2,4]triazol-1-yl] can be isolated by cooling to room temperature.

This process is highly-reproducible and the resulting crystalline product has good filtration.

A process for the preparation of the amorphous form of 4-[3,5-bis(2-hydroxyphenyl)-[1,2,4]triazol-1-yl]benzoic acid comprises the following steps:
  (a) dissolving the crystalline form of modification A or modification B of 4-[3,5-bis(2-hydroxyphenyl)-[1,2,4]triazol-1-yl]benzoic acid in a solvent, e.g. an aqueous solvent, e.g. water, or in a mixture of 50% organic solvent/50% aqueous medium, e.g. 50% water/50% methylbutylether, or 50% water/50% diethylether, or in a mixture of organic solvents, e.g. 50% toluene/50%acetonitrile, 50%n-hexane/50% toluene, or or 50% n-hexane/50% acetonitrile
  (b) fast evaporation of the solvent, e.g. under a stream of nitrogen
  (c) isolating the amorphous solid.

The above conditions on the selective preparation of the individual crystal forms and the amorphous form are not conclusive. In general, e.g., it is possible to vary parameters such as the weight ratio of the compound of formula (I) to the solvent.

The preferred form of this composition is solid 4-[3,5-bis(2-hydroxyphenyl)-[1,2,4]triazol-1-yl]benzoic acid powder suitable for use as an active ingredient in formulating pharmaceutical products. The reminder of the solid 4-[3,5-bis(2-hydroxyphenyl)-[1,2,4]triazol-1-yl]benzoic acid in the composition, i.e., 20% or less of the total weight of 4-[3,5-bis(2-hydroxyphenyl)-[1,2,4]triazol-1-yl]benzoic acid may be, e.g., crystalline forms of 4-[3,5-bis(2-hydroxyphenyl)-[1,2,4]triazol-1-yl]benzoic acid.

Also provided are pharmaceutical compositions containing a crystalline form A of 4-[3,5-bis(2-hydroxyphenyl)-[1,2,4]triazol-1-yl]benzoic acid and a pharmaceutically acceptable carrier.

Also provided are pharmaceutical compositions containing a crystalline form B of 4-[3,5-bis(2-hydroxyphenyl)-[1,2,4]triazol-1-yl]benzoic acid and a pharmaceutically acceptable carrier.

The invention provides a composition comprising solid 4-[3,5-bis(2-hydroxyphenyl)-[1,2,4]triazol-1-yl]benzoic acid in its crystalline form C or D or $S_B$, or C and D, or C and/or D and $S_B$.

The invention provides a composition containing 4-[3,5-bis(2-hydroxyphenyl)-[1,2,4]triazol-1-yl]benzoic acid, which is at least 80%, by total weight of 4-[3,5-bis(2-hydroxyphenyl)-[1,2,4]triazol-1-yl]benzoic acid in the composition, its crystalline form C or D. The preferred form of this composition is solid 4-[3,5-bis(2-hydroxyphenyl)-[1,2,4]triazol-1-yl]benzoic acid powder suitable for use as active ingredient in formulating pharmaceutical products. The remainder of 4-[3,5-bis(2-hydroxyphenyl)-[1,2,4]triazol-1-yl]benzoic acid in the composition, i.e., 20% or less of the total weight of 4-[3,5-bis(2-hydroxyphenyl)-[1,2,4]triazol-1-yl]benzoic acid may be, e.g., other crystalline forms of 4-[3,5-bis(2-hydroxyphenyl)-[1,2,4]triazol-1-yl]benzoic acid. In one specific embodiment, the composition contains at least 90% of the crystalline form C or D of 4-[3,5-bis(2-hydroxyphenyl)-[1,2,4]triazol-1-yl]benzoic acid with respect to the total weight of 4-[3,5-bis(2-hydroxyphenyl)-[1,2,4]triazol-1-yl]benzoic acid in the composition. In another specific embodiment, the composition contains at least 95% of the crystalline form C or D with respect to total weight of 4-[3,5-bis(2-hydroxyphenyl)-[1,2,4]triazol-1-yl]benzoic acid in the composition.

A process for the preparation of crystalline form C of 4-[3,5-bis(2-hydroxyphenyl)-[1,2,4]triazol-1-yl]benzoic acid is also provided. The process involves:
  (a) providing a solution 4-[3,5-bis(2-hydroxyphenyl)-[1,2,4]triazol-1-yl]benzoic acid in a mixture of protic and/or aprotic solvents, e.g. in THF/water/ethanol, e.g. (2:4:4), e.g. using the amorphous form of 4-[3,5-bis(2-hydroxyphenyl)-[1,2,4]triazol-1-yl]benzoic acid;
  (b) drying the solution of step (a),
  (c) suspending the dry precipitate obtained in step (b), e.g. in a mixture of solvents, e.g. a mixture comprising v/v of a solvent 1, e.g. acetonitrile, methanol, or dichloromethane, and of a solvent 2, e.g. n-hexane, toluene, or cyclohexane, e.g. under agitation, e.g. using a high-speed vortexer, e.g. at about 30, e.g. at 30 e.g. for about 2 hours, e.g. for 2 hours,
  (d) isolating the crystalline form C of 4-[3,5-bis(2-hydroxyphenyl)-[1,2,4]triazol-1-yl]benzoic acid, e.g. by evaporating the solution of step (c), e.g. at room temperature, e.g. under a stream of nitrogen.

In one embodiment, 4-[3,5-bis(2-hydroxyphenyl)-[1,2,4]triazol-1-yl]benzoic acid is dissolved in THF/ethanol, precipitated by addition of seeding crystals of the crystalline form C of 4-[3,5-bis(2-hydroxyphenyl)-[1,2,4]triazol-1-yl]benzoic acid and addition of ethanol as the anti-solvent, and crystalline form C of 4-[3,5-bis(2-hydroxyphenyl)-[1,2,4]triazol-1-yl]benzoic acid is obtained.

X-ray powder diffraction patterns was measured on a Bruker D8 Gadds Diffractometer, with CuK alpha radiation source, e.g. using a wavelength of 0.15406 nm. The X-ray diffraction pattern depicted in FIG. 9 is summarized in Table 3.

TABLE 3

Powder X-Ray Diffraction Peaks for the Form C Crystal Modification of 4-[3,5-bis(2-hydroxyphenyl)-[1,2,4]triazol-1-yl]benzoic acid

| ° deg 2 θ | d-space | Relative intensity (%) |
| --- | --- | --- |
| 9.2 | 9.577 | Weak (32) |
| 12.4 | 7.145 | Strong (88) |
| 13.2 | 6.719 | Strong (85) |
| 16.3 | 5.422 | Strong (100) |
| 18.3 | 4.836 | Medium (58) |
| 21.3 | 4.165 | Medium (58) |
| 22.2 | 4.002 | Medium (64) |
| 24.2 | 3.679 | Medium (42) |
| 25.1 | 3.539 | Strong (84) |

X-ray powder diffraction patterns was measured on a Bruker D8 Gadds Diffractometer, with CuK alpha radiation source, e.g. using a wavelength of 0.15406 nm. The X-ray diffraction pattern depicted in FIG. 11 is summarized in Table 4.

TABLE 4

Powder X-Ray Diffraction Peaks for the Form D Crystal Modification of 4-[3,5-bis(2-hydroxyphenyl)-[1,2,4]triazol-1-yl]benzoic acid

| ° deg 2 θ | d-space | Relative intensity (%) |
|---|---|---|
| 7.0 | 12.656 | Medium (52) |
| 9.4 | 9.450 | Medium (67) |
| 10.6 | 8.353 | Medium (49) |
| 11.3 | 7.793 | Medium (69) |
| 13.9 | 6.369 | Medium (44) |
| 15.0 | 5.902 | Strong (87) |
| 20.4 | 4.355 | Medium (72) |
| 21.4 | 4.156 | Strong (100) |

X-ray powder diffraction patterns was measured on a Bruker D8 Gadds Diffractometer, with CuK alpha radiation source, e.g. using a wavelength of 0.15406 nm. The X-ray diffraction pattern depicted in FIG. 13 is summarized in Table 5.

TABLE 5

Powder X-Ray Diffraction Peaks for the Form $S_B$ Crystal Modification of 4-[3,5-bis(2-hydroxyphenyl)-[1,2,4]triazol-1-yl]benzoic acid

| ° deg 2 θ | d-space | Relative intensity (%) |
|---|---|---|
| 9.4 | 9.356 | 23 |
| 10.0 | 8.810 | 40 |
| 11.3 | 7.846 | 100 |
| 12.8 | 6.903 | 23 |
| 15.0 | 5.894 | 70 |
| 16.1 | 5.489 | 33 |
| 22.1 | 4.021 | 38 |
| 24.3 | 3.660 | 44 |

It should be kept in mind that slight variations in observed 2θ angles or d-spacing values are expected based on the specific diffractometer employed, the analyst and the sample preparation technique. More variation is expected for the relative peak intensities. Identification of the exact crystalline form of a compound should be based primarily on observed 2 θ angles with lesser importance attributed to relative peak intensities. Some margin of error is present in each of the 2 θ angle assignments reported herein. The assigned margin of error, in a preferred variant, the crystalline forms C, D and $S_B$ of 4-[3,5-bis(2-hydroxyphenyl)-[1,2,4]triazol-1-yl]benzoic acid is approximately ±0.2° for each of the peak assignments.

One or more of physical properties and/or spectroscopic properties can be the basis for characterizing the crystal or polymorphic forms of 4-[3,5-bis(2-hydroxyphenyl)-[1,2,4]triazol-1-yl]benzoic acid.

A process for the preparation of crystalline form D of 4-[3,5-bis(2-hydroxyphenyl)-[1,2,4]triazol-1-yl]benzoic acid involves the following steps:
(a) suspending the modification A material in a solvent, e.g. a mixture of diethylamine/cyclohexane v/v (1/1),
(b) mixing the suspension of step (a), e.g. at 30° C. e.g. for 2 hours,
(c) filtering the mixture of step (b), e.g. on a 0.2 mm filter, e.g. with regular cellulose membrane,
(d) evaporating the solution of step (c), e.g. under stream of $N_2$,
(e) isolating the crystals of crystalline form D of 4-[3,5-bis (2-hydroxyphenyl)-[1,2,4]triazol-1-yl]benzoic acid.

A process for the preparation of the crystalline form $S_B$ of 4-[3,5-bis(2-hydroxyphenyl)-[1,2,4]triazol-1-yl]benzoic acid comprises the following steps:
(a) suspending the crystalline form of modification A of 4-[3,5-bis(2-hydroxyphenyl)-[1,2,4]triazol-1-yl]benzoic acid in a solvent, e.g. in DMF,
(b) the suspension of step (a) is sonicated, e.g. for about 15 min, e.g. for 15 min, and filtered, e.g. on 0.2 um regular cellular membrane,
(c) solution of step (b) is added to water,
(d) the precipitate obtained in step (c) is filtered and dried, e.g. under N2,
(e) the crystalline form $S_B$ is isolated.

The above conditions on the selective preparation of the individual crystal forms and the amorphous form are not conclusive. In general, e.g., it is possible to vary parameters such as the weight ratio of the compound of formula (I) to the solvent.

Also provided are pharmaceutical compositions containing a crystalline form C of 4-[3,5-bis(2-hydroxyphenyl)-[1,2,4]triazol-1-yl]benzoic acid and a pharmaceutically acceptable carrier.

Also provided are pharmaceutical compositions containing a crystalline form D of 4-[3,5-bis(2-hydroxyphenyl)-[1,2,4]triazol-1-yl]benzoic acid and a pharmaceutically acceptable carrier.

In addition to the active compound, the pharmaceutical composition include one or more pharmaceutically acceptable carriers, also known as excipients, which ordinarily lack pharmaceutical activity, but have various useful properties which may, e.g., enhance the stability, sterility, bioavailability and ease of formulation of a pharmaceutical composition. These carriers are pharmaceutically acceptable, meaning that they are not harmful to humans or animals when taken appropriately and are compatible with other ingredients in a given formulation. The carriers may be solid, semi-solid or liquid, and may be formulated with the compound in bulk, but ultimately in the form of a unit-dose formulation, i.e., a physically discrete until containing a specific amount of active ingredient, such as a tablet or capsule. The pharmaceutical compositions may include, in addition to a compound of this invention, one or more active pharmaceutical compounds.

The pharmaceutical compositions may be in the form of suspensions, solutions, elixirs, aerosols or solid dosage forms.

The pharmaceutical compositions are contemplated in various formulations suitable for various modes of administration including, but not limited to, inhalation, oral, rectal, parenteral (including subcutaneous, intradermal, intramuscular and intravenous), implantable and transdermal administration. The most suitable route of administration in an given case depends on the duration of the subject's condition, the length of treatment desired, the nature and severity of the condition being treated, and the particular formulation that is being used. The formulations may be in bulk or in unit dosage form, and may be prepared by methods well-known in the art for a given formulation.

The amount of active ingredient included in a unit dosage form depends on the type of formulation in which the active ingredient is presented. A pharmaceutical composition will generally contain about 0.1% by weight to about 99% by weight of the active ingredient, preferably about 1% by weight to 50% by weight for oral administration and about 0.2% by weight to about 20% by weight for parenteral administration.

Formulations suitable for oral administration include capsules (hard and soft), cachets, lozenges, syrups, suppositories and tablets, each containing a predetermined amount of the active compound; as a powder or granules, as a solution or a suspension in an aqueous or non-aqueous liquid; or as an oil-in-water or water-in-oil emulsion. Such formulations may be prepared by any suitable method of pharmacy that includes the step of bringing into association the active compound and a suitable carrier or carriers.

Oral administration is the preferred route of administration of the present invention.

In another aspect, the invention also provides methods of treatment using the compounds and the pharmaceutical compositions of this invention.

The compounds and compositions of this invention may be administered to a subject in an amount effective to be used for the treatment of an excess of iron in the human or animal body and/or disorders related to excess of iron in such subjects.

The present invention relates especially to crystalline form A and crystalline form B and crystalline form C and crystalline form D of 4-[3,5-bis(2-hydroxyphenyl)-[1,2,4]triazol-1-yl]benzoic acid disclosed herein for the treatment of one of the said disorders or in the preparation of a pharmacological agent for the treatment thereof. Various disorders of warm-blooded animals are linked with an excess of metals, in particular trivalent metals, in the body tissues. For example aluminium in dialysis encephalopathy and osteomalacia, as well as in Alzheimer's disease. In other illnesses, in particular of man, an excess of iron occurs in the various tissues. This is designated as iron overload (formerly haemosiderosis). It occurs, for example, after parenteral administration of iron (especially repeated blood transfusions) or after increased uptake of iron from the gastrointestinal tract. Repeated transfusions are necessary in serious anaemias, especially in thalassaemia major, the severe form of β-thalassaemia, but also in other anaemias. Increased iron absorption from the gastrointestinal tract either takes place primarily, e.g. on account of a genetic defect (so-called haemochromatosis), or secondarily, such as after anaemias in which blood transfusions are not necessary, for example thalassaemia intermedia, a milder form of β-thalassaemia. A reduction in the iron(III) concentration is also of interest for the treatment of disorders due to iron(III)-dependent microorganisms and parasites, which is of key importance not only in human medicine, such as in particular in malaria, but also in veterinary medicine. Complexing of other metals, in particular trivalent metals, can also be used for excretion thereof from the organism.

The invention relates also to a process for the treatment of warm-blooded animals suffering from said disorders wherein a quantity of the crystalline form A of 4-[3,5-bis(2-hydroxyphenyl)-[1,2,4]triazol-1-yl]benzoic acid and/or crystalline form B of 4-[3,5-bis(2-hydroxyphenyl)-[1,2,4]triazol-1-yl]benzoic acid and/or crystalline form C of 4-[3,5-bis(2-hydroxyphenyl)-[1,2,4]triazol-1-yl]benzoic acid and/or crystalline form D of 4-[3,5-bis(2-hydroxyphenyl)-[1,2,4]triazol-1-yl]benzoic acid, which is effective against the disease concerned is administered to warm-blooded animals in need of such treatment.

The invention relates moreover to the use of the crystalline form A of 4-[3,5-bis(2-hydroxyphenyl)-[1,2,4]triazol-1-yl]benzoic acid and/or crystalline form B of 4-[3,5-bis(2-hydroxyphenyl)-[1,2,4]triazol-1-yl]benzoic acid and/or crystalline form C of 4-[3,5-bis(2-hydroxyphenyl)-[1,2,4]triazol-1-yl]benzoic acid and/or crystalline form D of 4-[3,5-bis(2-hydroxyphenyl)-[1,2,4]triazol-1-yl]benzoic acid for the treatment of an excess of iron in the human or animal body and/or a disorder related to the excess of iron, or for the preparation of pharmaceutical compositions for use in treating the human or animal body, especially in disorders related to the excess of iron.

The dosage of the active ingredient can depend on various factors, such as activity and duration of action of the active ingredient, severity of the illness to be treated or its symptoms, manner of administration, warm-blooded animal species, sex, age, weight and/or individual condition of the warm-blooded animal. The doses to be administered daily in the case of oral administration are between 10 and approximately 120 mg/kg, in particular 20 and approximately 80 mg/kg, and for a warm-blooded animal having a body weight of approximately 40 kg, preferably between approximately 400 mg and approximately 4,800 mg, in particular approximately 800 mg to 3,200 mg, which is expediently divided into 2 to 12 individual doses.

The invention relates also to pharmaceutical preparations which comprise an effective amount, especially an effective amount for prevention or treatment of one of the said diseases, especially a disorder related to the excess of iron, of the crystalline form A of 4-[3,5-bis(2-hydroxyphenyl)-[1,2,4]triazol-1-yl]benzoic acid and/or crystalline form B of 4-[3,5-bis(2-hydroxyphenyl)-[1,2,4]triazol-1-yl]benzoic acid and/or crystalline form C of 4-[3,5-bis(2-hydroxyphenyl)-[1,2,4]triazol-1-yl]benzoic acid and/or crystalline form D of 4-[3,5-bis(2-hydroxyphenyl)-[1,2,4]triazol-1-yl]benzoic acid, together with pharmaceutically acceptable carriers which are suitable for topical; enteral, e.g. oral or rectal; or parenteral administration and may be inorganic or organic and solid or liquid.

Pharmaceutical preparations for enteral or parenteral administration are, for example, those in unit dose forms, such as sugar-coated tablets, tablets, dispersible tablets, effervescent tablets, capsules, suspendable powders, suspensions or suppositories, or ampoules. These are prepared in a manner known per se, e.g. by means of conventional pan-coating, mixing, granulation or lyophilization processes. Pharmaceutical preparations for oral administration can thus be obtained by combining the active ingredient with solid carriers, if desired granulating a mixture obtained and processing the mixture or granules, if desired or necessary, after addition of suitable adjuncts to give tablets or sugar-coated tablet cores.

Suitable carriers are, in particular, fillers such as sugars, e.g. lactose, sucrose, mannitol or sorbitol, cellulose preparations and/or calcium phosphates, e.g. tricalcium phosphate or calcium hydrogen phosphate, furthermore binders, such as starch pastes, using, for example, maize, wheat, rice or potato starch, gelatin, tragacanth, methylcellulose and/or polyvinylpyrrolidone, and, if desired, disintegrants, such as the abovementioned starches, furthermore carboxymethyl starch, crosslinked polyvinylpyrrolidone, agar or alginic acid or a salt thereof, such as sodium alginate. Adjuncts are primarily flow-regulating and lubricating agents, e.g. salicylic acid, talc, stearic acid or salts thereof, such as magnesium or calcium stearate, and/or polyethylene glycol. Sugar-coated tablet cores are provided with suitable, if desired enteric, coatings, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of enteric coatings, solutions of suitable cellulose preparations, such as acetylcellulose phthalate or hydroxypropylmethylcellulose phthalate. Colorants or pigments, e.g. for the identification or the marking of various doses of active ingredient, can be added to the tablets or sugar-coated tablet coatings.

Dispersible tablets are tablets which rapidly disintegrate in a comparatively small amount of liquid, e.g. water, and which, if desired, contain flavourings or substances for masking the taste of the active ingredient. They can advantageously be employed for the oral administration of large individual doses, in which the amount of active ingredient to be administered is so large that on administration as a tablet which is to be swallowed in undivided form or without chewing that it can no longer be conveniently ingested, in particular by children. Further orally administrable pharmaceutical preparations are hard gelatin capsules and also soft, closed capsules of gelatin and a plasticizer, such as glycerol or sorbitol. The hard gelatin capsules can contain the active ingredient in the form of granules, e.g. as a mixture with fillers, such as lactose, binders, such as starches, and/or glidants, such as talc or magnesium stearate, and, if desired, stabilizers. In soft capsules, the active ingredient is preferably dissolved or suspended in suitable liquids, such as fatty oils, liquid paraffin or liquid polyethylene glycols, it also being possible to add stabilizers.

Moreover, suspendable powders, e.g. those which are described as "powder in bottle", abbreviated "PIB", or ready-to-drink suspensions, are suitable for an oral administration form. For this form, the active ingredient is mixed, for example, with pharmaceutically acceptable surface-active substances, for example, sodium lauryl sulfate or polysorbate, suspending auxiliaries, e.g. hydroxypropylcellulose, hydroxypropylmethylcellulose or another known from the prior art and previously described, for example, in "Handbook of Pharmaceutical Excipients", pH regulators, such as citric or tartaric acid and their salts or a USP buffer and, if desired, fillers, e.g. lactose, and further auxiliaries, and dispensed into suitable vessels, advantageously single-dose bottles or ampoules. Immediately before use, a specific amount of water is added and the suspension is prepared by shaking. Alternatively, the water can also be added even before dispensing.

Rectally administrable pharmaceutical preparations are, for example, suppositories which consist of a combination of the active ingredient with a suppository base. A suitable suppository base is, for example, natural or synthetic triglycerides, paraffin hydrocarbons, polyethylene glycols or higher alkanols. Gelatin rectal capsules can also be used which contain a combination of the active ingredient with a base substance. Possible base substances are, for example, liquid triglycerides, polyethylene glycols or paraffin hydrocarbons.

For parenteral administration, aqueous solutions of an active ingredient in water-soluble form, e.g. of a water-soluble salt, are primarily suitable; furthermore suspensions of the active ingredient, such as appropriate oily injection suspensions, suitable lipophilic solvents or vehicles, such as fatty oils, e.g. sesame oil, or synthetic fatty acid esters, e.g. ethyl oleate or triglycerides, being used, or aqueous injection suspensions which contain viscosity-increasing substances, e.g. sodium carboxymethylcellulose, sorbitol and/or dextran, and, if desired, also stabilizers.

The invention is further defined by reference to the following examples describing in detail the preparation of the compound and the compositions of the present invention, as well as their utility. It will be apparent to those skilled in the art, that many modifications, both to materials, and methods, may be practiced with out departing from the purpose and interest of this invention. The examples that follow are not intended to limit the scope of the invention as defined hereinabove or as claimed below.

EXAMPLES

Example 1

Preparation of crystalline form A of 4-[3,5-bis(2-hydroxyphenyl)-[1,2,4]triazol-1-yl]benzoic acid using THF/ethanol and HXF.

Example 2

Preparation of crystalline form A of 4-[3,5-bis(2-hydroxyphenyl)-[1,2,4]triazol-1-yl]benzoic acid using toluene and THF.

Example 3

Preparation of crystalline form A of 4-[3,5-bis(2-hydroxyphenyl)-[1,2,4]triazol-1-yl]benzoic acid using Methanol/THF.

Example 4

Preparation of crystalline form A of 4-[3,5-bis(2-hydroxyphenyl)-[1,2,4]triazol-1-yl]benzoic acid using formic acid and ethanol.

Example 5

Preparation of crystalline form A of 4-[3,5-bis(2-hydroxyphenyl)-[1,2,4]triazol-1-yl]benzoic acid using methanol/THF and water.

Example 6

Preparation of crystalline form A of 4-[3,5-bis(2-hydroxyphenyl)-[1,2,4]triazol-1-yl]benzoic acid using methanol/THF and HXF.

Example 7

Preparation of crystalline form B of 4-[3,5-bis(2-hydroxyphenyl)-[1,2,4]triazol-1-yl]benzoic acid from recrystallization of the amorphous form at temperature above 100° C.

Example 8

Preparation of crystalline form B of 4-[3,5-bis(2-hydroxyphenyl)-[1,2,4]triazol-1-yl]benzoic acid from recrystallization of the amorphous form at temperature above 140° C.

Example 9

Preparation of Crystalline Form C
4-[3,5-bis(2-hydroxyphenyl)-[1,2,4]triazol-1-yl]benzoic acid is dissolved in THF/water/Ethanol, e.g. (2:4:4). Said solution is dispensed into a 96-well block to have a total amount of drug substance of 2 mg per well. The solution is then allowed to dry by flushing with nitrogen at room temperature. The dry precipitate is resuspended with either a mixture of 125 microL of a solvent 1, e.g. acetonitrile, methanol or dichloromethane and 125 microL of solvent 2, e.g. n-hexane, toluene or cyclohexane. The suspension or solution is agitated using high-speed vortexer, e.g. at about 30° C., e.g.

30° C., e.g. for about 2 hours, e.g. 2 hours. The solution is evaporated, e.g. at room temperature, e.g. under a stream of nitrogen. The Modification C is isolated.

Example 10

Preparation of Crystalline Form D

About 50 mg of the modification A of 4-[3,5-bis(2-hydroxyphenyl)-[1,2,4]triazol-1-yl]benzoic acid are suspended in 5 ml of a mixture of diethylamine/cyclohexane v/v (1/1). The suspension is then mixed 2 hours at 30° C. and filtrated on a 0.2 µm filter with regular cellulose membrane. Then the solution is allowed to evaporate under stream of $N_2$. The solid precipitate is isolated and analyzed by XRPD using a Bruker D8 Gadds Diffractometer.

What is claimed is:

1. A compound which is a crystalline form D of 4-[3,5-bis(2-hydroxyphenyl)-[1,2,4]triazol-1-yl]benzoic acid and which shows on X-ray diffraction peaks at angles of refraction 2 theta (θ), of 7.0 and 9.4±0.2 degrees.

2. The compound according to 1, having an x-ray diffraction pattern, expressed in terms of 2 θ angles, that further includes three or more peaks selected from the group of peaks at 10.6, 11.3, 13.9, 15.0, 20.4, 21.4±0.2 degrees.

3. The compound according to claim 1 having the same X-ray diffraction pattern as shown in FIG. 11.

4. The crystalline form of 4-[3,5-bis(2-hydroxyphenyl)-[1,2,4]triazol-1-yl]benzoic acid according to claim 1, which is present in essentially pure form.

5. A crystalline form of 4-[3,5-bis(2-hydroxyphenyl)-[1,2,4]triazol-1-yl]benzoic acid which shows an X-ray diffraction diagram of the type shown in FIG. 11, in which the relative peak intensities of each peak do not deviate by more than 10% from the relative peak intensities in the diagram shown in FIG. 11.

6. A composition comprising 4-[3,5-bis(2-hydroxyphenyl)-[1,2,4]triazol-1-yl]benzoic acid as a solid, wherein at least 80% by weight of said solid 4-[3,5-bis(2-hydroxyphenyl)-[1,2,4]triazol-1-yl]benzoic acid is the crystalline form D according to claim 1.

7. The composition according to claim 6, wherein at least 90% by weight of said solid 4-[3,5-bis(2-hydroxyphenyl)-[1,2,4]triazol-1-yl]benzoic acid is the crystalline form D.

8. The composition according to claim 6, wherein at least 95% by weight of said solid 4-[3,5-bis(2-hydroxyphenyl)-[1,2,4]triazol-1-yl]benzoic acid is the crystalline form D.

* * * * *